(12) United States Patent
Yanai

(10) Patent No.: US 12,158,412 B2
(45) Date of Patent: Dec. 3, 2024

(54) CONCENTRATION MEASURING METHOD OF OPTICALLY ACTIVE SUBSTANCE AND CONCENTRATION MEASURING DEVICE OF OPTICALLY ACTIVE SUBSTANCE

(71) Applicant: FUJIFILM Corporation, Tokyo (JP)

(72) Inventor: Yujiro Yanai, Minamiashigara (JP)

(73) Assignee: FUJIFILM Corporation, Tokyo (JP)

( * ) Notice: Subject to any disclaimer, the term of this patent is extended or adjusted under 35 U.S.C. 154(b) by 181 days.

(21) Appl. No.: 18/161,245

(22) Filed: Jan. 30, 2023

(65) Prior Publication Data

US 2023/0213436 A1 Jul. 6, 2023

Related U.S. Application Data

(63) Continuation of application No. PCT/JP2021/025166, filed on Jul. 2, 2021.

(30) Foreign Application Priority Data

Jul. 31, 2020 (JP) ................................. 2020-130675

(51) Int. Cl.
*G01N 21/21* (2006.01)
*G01N 33/66* (2006.01)

(52) U.S. Cl.
CPC ............. *G01N 21/21* (2013.01); *G01N 33/66* (2013.01); *G01N 2021/215* (2013.01);
(Continued)

(58) Field of Classification Search
CPC ................ A61B 5/14532; A61B 3/117; G01N 2021/215; G01N 21/21; G01N 21/23;
(Continued)

(56) References Cited

U.S. PATENT DOCUMENTS 5,535,743 A 7/1996 Backhaus et al.
2003/0233036 A1 12/2003 Ansari et al.
(Continued)

FOREIGN PATENT DOCUMENTS

JP 6-237898 A 8/1994
JP 2003-254901 A 9/2003

OTHER PUBLICATIONS

International Preliminary Report on Patentability and English translation of the Written Opinion of the International Searching Authority for International Application No. PCT/JP2021/025166, dated Feb. 9, 2023.
(Continued)

*Primary Examiner* — Tri T Ton
(74) *Attorney, Agent, or Firm* — Birch, Stewart, Kolasch & Birch, LLP

(57) ABSTRACT

Provided are a concentration measuring method of an optically active substance and a concentration measuring device of an optically active substance, which can easily and accurately measure a concentration of the optically active substance in aqueous humor. The concentration measuring method of an optically active substance includes: a first step of measuring a polarization state of a first reflected light that is obtained by irradiating an aqueous humor in an eye with an incidence light which is polarized and reflecting the incidence light at an interface between the aqueous humor and a lens, in which the polarization state of the first reflected light is measured by irradiating a first incidence light such that an angle between a normal line to a point where the incidence light intersects a surface of the lens, and the incidence light is equal to or smaller than a Brewster angle; a second step of measuring a polarization state of a second reflected light by irradiating with a second incidence light such that an angle of the incidence light is equal to or larger than the Brewster angle; a third step of calculating an
(Continued)

optical rotation of the aqueous humor with information on the polarization state of the first reflected light and information on the polarization state of the second reflected light; and a fourth step of calculating a concentration of an optically active substance in the aqueous humor from the optical rotation of the aqueous humor.

20 Claims, 10 Drawing Sheets

(52) U.S. Cl.
CPC . *G01N 2201/061* (2013.01); *G01N 2201/068* (2013.01); *G01N 2201/124* (2013.01)

(58) Field of Classification Search
CPC ....... G01N 2201/061; G01N 2201/068; G01N 2201/124; G01N 33/66
See application file for complete search history.

(56) References Cited

U.S. PATENT DOCUMENTS

2011/0105868 A1    5/2011  Westphal
2018/0333048 A1*  11/2018  Harris ..................... A61B 3/10

OTHER PUBLICATIONS

International Search Report for International Application No. PCT/JP2021/025166, dated Sep. 14, 2021, with English translation.

* cited by examiner

CONCENTRATION MEASURING METHOD OF OPTICALLY ACTIVE SUBSTANCE AND CONCENTRATION MEASURING DEVICE OF OPTICALLY ACTIVE SUBSTANCE

CROSS-REFERENCE TO RELATED APPLICATIONS

This application is a Continuation of PCT International Application No. PCT/JP2021/025166 filed on Jul. 2, 2021, which claims priority under 35 U.S.C. § 119(a) to Japanese Patent Application No. 2020-130675 filed on Jul. 31, 2020. Each of the above applications is hereby expressly incorporated by reference, in their entirety, into the present application.

BACKGROUND OF THE INVENTION

1. Field of the Invention

The present invention relates to a concentration measuring method of an optically active substance and a concentration measuring device of an optically active substance.

2. Description of the Related Art

As a noninvasive blood glucose level measuring method, it is proposed that a glucose concentration is measured by irradiating an aqueous humor in the eye with polarized light and measuring an optical rotation of the polarized light which passes through the aqueous humor and is reflected at an interface with a lens, using optical characteristics depending on the glucose concentration.

For example, JP1993-237898A (JP-H6-237898A) discloses a device for an in vivo measurement of an optical property of an aqueous humor in an anterior chamber of a patient's eye, which includes: a light source unit for irradiating light into the anterior chamber along a primary light path having a central ray; a detection unit for detecting the light originating from the light source unit and light issuing from the anterior chamber along a secondary light path having a central ray to generate a measurement signal representative of a detected light; and a signal processing unit coupled to the detection unit and for measuring optical properties based on the measurement signal, in which the device is disposed in front of the patient's eye, and the central rays of the primary light path and the secondary light path are arranged to be at equal and opposite angles from a normal to a front interface of an eye lens, so that a specular reflection from the interface is detected by the detection unit.

SUMMARY OF THE INVENTION

In the method of measuring the glucose concentration by irradiating the aqueous humor in the eye with polarized light and measuring the optical rotation of the polarized light which has passed through the aqueous humor, the polarized light passes through cornea of the eye as it enters the aqueous humor and as it exits the lens. The cornea has optical characteristics that are more likely to change the polarization than the aqueous humor. Therefore, for example, due to variation in optical rotation caused by the cornea of each patient, the optical rotation caused by the aqueous humor cannot be measured accurately, and as a result, there is a problem that measurement accuracy of the glucose concentration in the aqueous humor is low.

An object of the present invention is to provide a concentration measuring method of an optically active substance and a concentration measuring device of an optically active substance, which can easily and accurately measure a concentration of the optically active substance in aqueous humor.

In order to solve the problems, the present invention has the following configuration.

[1] A concentration measuring method of an optically active substance, comprising:
  a first step of measuring a polarization state of a first reflected light that is obtained by irradiating an aqueous humor in an eye with a first incidence light which is polarized and reflecting the first incidence light at an interface between the aqueous humor and a lens, in which the polarization state of the first reflected light is measured by performing the irradiation with the first incidence light such that an angle $\theta_1$ between a normal line to a tangent plane at a point where the first incidence light intersects a surface of the lens, and the first incidence light is equal to or smaller than a Brewster angle;
  a second step of measuring a polarization state of a second reflected light that is obtained by irradiating the aqueous humor in the eye with a second incidence light which is polarized and reflecting the second incidence light at the interface between the aqueous humor and the lens, in which the polarization state of the second reflected light is measured by performing the irradiation with the second incidence light such that an angle $\theta_2$ between a normal line to a tangent plane at a point where the second incidence light intersects the surface of the lens, and the second incidence light is equal to or larger than the Brewster angle;
  a third step of calculating an optical rotation of the aqueous humor with information on the polarization state of the first reflected light, which is obtained in the first step, and information on the polarization state of the second reflected light, which is obtained in the second step; and
  a fourth step of calculating a concentration of an optically active substance in the aqueous humor from the optical rotation of the aqueous humor.

[2] The concentration measuring method of an optically active substance according to [1],
  in which the first step is performed a plurality of times under conditions in which the angle $\theta_1$ between the normal line and the first incidence light is different, so that a plurality of pieces of the information on the polarization state of the first reflected light in the first step are acquired, and
  the third step is performed with the plurality of pieces of the information acquired.

[3] The concentration measuring method of an optically active substance according to [1] or [2],
  in which the second step is performed a plurality of times under conditions in which the angle $\theta_2$ between the normal line and the second incidence light is different, so that a plurality of pieces of the information on the polarization state of the second reflected light in the second step are acquired, and
  the third step is performed with the plurality of pieces of the information acquired.

[4] The concentration measuring method of an optically active substance according to any one of [1] to [3],
  in which the first step is performed a plurality of times while changing a wavelength of the first incidence light, so that a plurality of pieces of the information on the polarization state of the first reflected light in the first step are acquired, and the third step is performed with the plurality of pieces of the information acquired.

[5] The concentration measuring method of an optically active substance according to any one of [1] to [4], in which the second step is performed a plurality of times while changing a wavelength of the second incidence light, so that a plurality of pieces of the information on the polarization state of the second reflected light in the second step are acquired, and the third step is performed with the plurality of pieces of the information acquired.

[6] The concentration measuring method of an optically active substance according to any one of [1] to [5], in which the angle $\theta_2$ between the normal line and the second incidence light in the second step is more than the Brewster angle.

[7] The concentration measuring method of an optically active substance according to any one of [1] to [6], in which the optically active substance is glucose.

[8] The concentration measuring method of an optically active substance according to any one of [1] to [7], in which, in at least one of the first step or the second step, a two-dimensional sensor in which light receiving sections for receiving the reflected light are two-dimensionally arranged is used.

[9] The concentration measuring method of an optically active substance according to any one of [1] to [8], in which, in the third step, information on optical characteristics of a cornea of the eye is acquired with the information on the polarization state of the first reflected light, which is obtained in the first step, and the optical rotation of the aqueous humor is calculated with the information on the optical characteristics of the cornea and the information on the polarization state of the second reflected light, which is obtained in the second step.

[10] A concentration measuring device of an optically active substance, which is for performing the concentration measuring method of an optically active substance according to any one of [1] to [9], the concentration measuring device comprising:

a light source for irradiating an incidence light which is polarized to an aqueous humor in an eye;

a measuring unit for measuring a polarization state of a reflected light obtained by reflecting the incidence light at an interface between the aqueous humor and a lens;

a control unit for controlling an incidence angle of the incidence light; and a calculation unit for calculating an optical rotation of the aqueous humor using information on the polarization state of the reflected light, which is measured by the measuring unit.

[11] The concentration measuring device of an optically active substance according to [10], in which the light source has a light emitting element and a polarizing plate, the measuring unit has a polarizing plate and a light receiving element, and at least one of the light source or the measuring unit has a phase difference plate.

[12] The concentration measuring device of an optically active substance according to [11], in which the light receiving element has a two-dimensional sensor in which light receiving sections for receiving the reflected light are two-dimensionally arranged.

According to the present invention, it is possible to provide a concentration measuring method of an optically active substance and a concentration measuring device of an optically active substance, which can easily and accurately measure a concentration of the optically active substance in aqueous humor.

DESCRIPTION OF THE PREFERRED EMBODIMENTS

Hereinafter, a concentration measuring method of an optically active substance and a concentration measuring device of an optically active substance according to embodiments of the present invention will be described in detail on the basis of suitable examples shown in the accompanying drawings.

In the present specification, a numerical range represented by "to" means a range including numerical values before and after "to" as a lower limit value and an upper limit value.

In the present specification, "same", "equal", and the like include an error range generally accepted in the technical field.

[Concentration Measuring Method of Optically Active Substance]

The concentration measuring method of an optically active substance according to the embodiment of the present invention is a concentration measuring method of an optically active substance, which includes:

a first step of measuring a polarization state of a first reflected light that is obtained by irradiating an aqueous humor in an eye with a first incidence light which is polarized and reflecting the first incidence light at an interface between the aqueous humor and a lens, in which the polarization state of the first reflected light is measured by performing the irradiation with the first incidence light such that an angle $\theta_1$ between a normal line to a tangent plane at a point where the first incidence light intersects a surface of the lens, and the first incidence light is equal to or smaller than a Brewster angle;

a second step of measuring a polarization state of a second reflected light that is obtained by irradiating the aqueous humor in the eye with a second incidence light which is polarized and reflecting the second incidence light at the interface between the aqueous humor and the lens, in which the polarization state of the second reflected light is measured by performing the irradiation with the second incidence light such that an angle $\theta_2$ between a normal line to a tangent plane at a point where the second incidence light intersects the surface of the lens, and the second incidence light is equal to or larger than the Brewster angle;

a third step of calculating an optical rotation of the aqueous humor with information on the polarization state of the first reflected light, which is obtained in the first step, and information on the polarization state of the second reflected light, which is obtained in the second step; and a fourth step of calculating a concentration of an optically active substance in the aqueous humor from the optical rotation of the aqueous humor.

<First Step>

Figure 1:
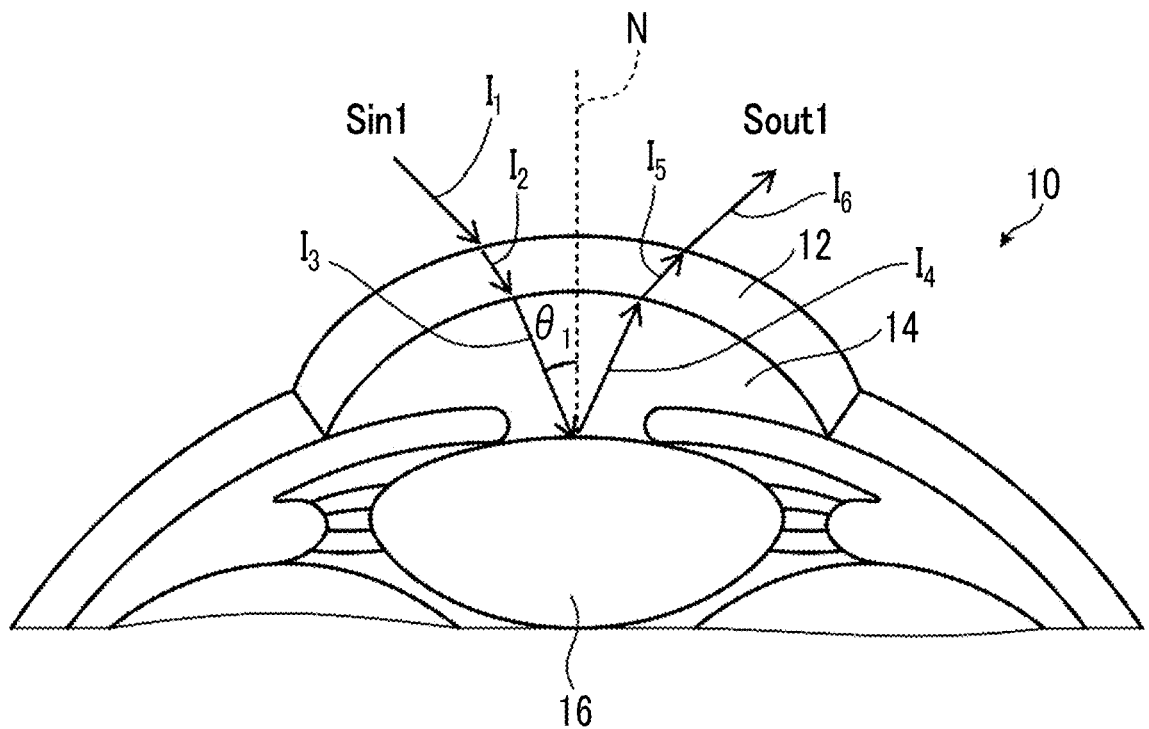
FIG. 1 is a conceptual diagram for explaining a first step of a concentration measuring method of an optically active substance according to the embodiment of the present invention.

FIG. 1 shows a conceptual diagram for explaining the first step of the concentration measuring method of an optically active substance according to the embodiment of the present invention.

The first step is a step of measuring, with a measuring unit (not shown), a polarization state a reflected light Sout1, that a first incidence light Sin1 which is polarized is incident from a light source (not shown) toward an aqueous humor 14 of an eye 10 and the reflected light Sout1 is emitted from the eye 10 after being reflected at an interface between the aqueous humor 14 and a lens 16.

Specifically, first, the first incidence light Sin1 emitted from the light source passes through air and is incident on a cornea 12 as indicated by an arrow $I_1$. The light incident on the cornea 12 passes through the cornea 12 and is incident on the aqueous humor 14 as indicated by an arrow $I_2$. The light incident on the aqueous humor 14 reaches the lens 16 through the aqueous humor 14 and is reflected at the interface between the aqueous humor 14 and the lens 16 as indicated by an arrow $I_3$. The reflected light passes through the aqueous humor 14 and is incident on the cornea 12 as indicated by an arrow $I_4$. The light incident on the cornea 12 passes through the cornea 12 and is emitted from the eye 10 as indicated by an arrow $I_5$. The emitted light (arrow $I_6$) is incident on the measuring unit. The measuring unit measures the polarization state of the first reflected light Sout1.

The measuring unit for measuring the polarization state of the reflected light will be described in detail later. The measurement of the polarization state is preferably performed with a two-dimensional sensor in which light receiving sections for receiving the reflected light are two-dimensionally arranged.

Figure 2:
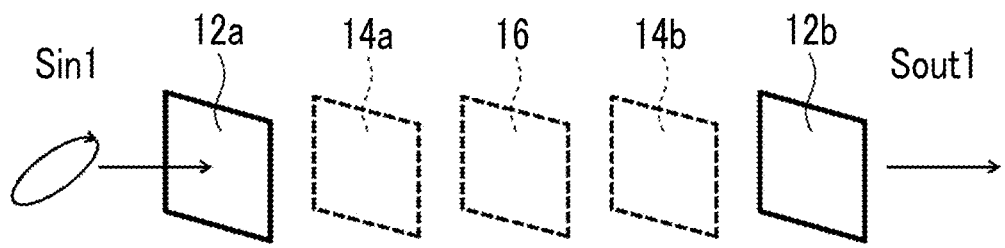
FIG. 2 is a conceptual diagram for explaining a calculation model in the first step.

In such a first step, as the light travels, the polarization state changes due to influence of the cornea 12, the aqueous humor 14, and the reflection. FIG. 2 shows a model for calculating the change in polarization state of light in the first step. FIG. 2 indicates that the incidence light Sin1 passes through a cornea 12a on the incident side, an aqueous humor 14a on the incident side, an aqueous humor 14b on the reflecting side, and a cornea 12b on the reflecting side in this order from the left side of the drawing, and is emitted as the reflected light Sout1.

Each of the cornea 12 and the aqueous humor 14 has optical characteristics which change a polarization state of light, specifically, optical activity. The optical activity is an optical characteristic that causes an action of rotating a polarization plane of incident linearly polarized light. Therefore, in a case where the first incidence light Sin1 passes through the cornea 12a on the incident side, the aqueous humor 14a on the incident side, the aqueous humor 14b on the reflecting side, and the cornea 12b on the reflecting side, is emitted as the first reflected light Sout1 with its polarization plane rotated at each site.

Figure 3:
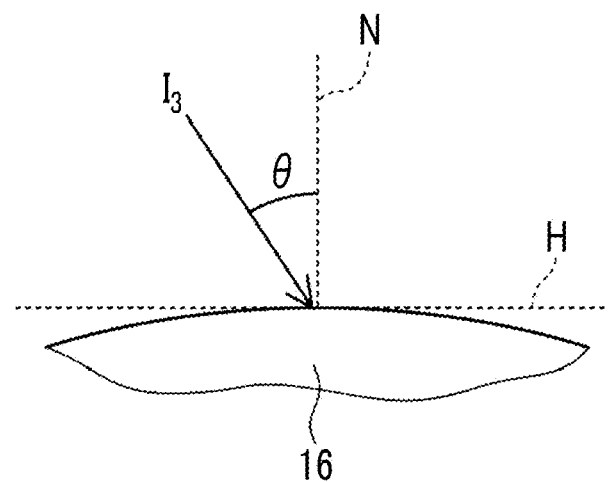
FIG. 3 is a diagram for explaining an angle $\theta$.

Here, in the first step, an angle $\theta_1$ of the first incidence light Sin1 in a case where the incidence light Sin1 is reflected at the interface between the aqueous humor 14 and the lens 16 is equal to or smaller than the Brewster angle. As shown in FIG. 3, the angle $\theta$ of the incidence light is an angle between a normal line N to a tangent plane H which is defined at a point where the incidence light intersects a surface (interface) of the lens 16, and a traveling direction (arrow $I_3$) of the incidence light. In the following description, an angle of the first incidence light Sin1 in the first step is denoted by $\theta_1$, and an angle of a second incidence light Sin2 in the second step is denoted by $\theta_2$. In addition, a Brewster angle $\theta_B$ is an angle represented by $\tan\theta_B = nt/ni$, in which a refractive index of a medium (aqueous humor 14 in FIG. 3) on the incident side is denoted by ni, and a refractive index of a medium (lens 16 in FIG. 3) on the reflecting side is denoted by nt.

In a case where the angle $\theta_1$ of the first incidence light Sin1 is equal to or smaller than the Brewster angle, when the first incidence light Sin1 is incident on the interface between the aqueous humor 14 and the lens 16, since the refractive index of the lens is higher than that of the aqueous humor, a phase of s-polarization is shifted by $\pi$ and a phase of p-polarization is not shifted. An incident surface is a surface perpendicular to a reflecting surface and including the incidence ray and the reflected ray.

Therefore, the angle (optical rotation) at which a polarization plane is rotated due to optical activity of the aqueous humor 14 in a case where light passes through the aqueous humor 14 (arrow $I_3$) before being reflected at the interface between the aqueous humor 14 and the lens 16 is canceled by the optical rotation due to optical activity of the aqueous humor 14 in a case where the reflected light passes through the aqueous humor 14 (arrow $I_4$). As a result, the optical rotation due to passing through the aqueous humor 14 is approximately 0.

On the other hand, a change in polarization due to birefringence of the cornea 12 in a case where light passes through the cornea 12 (arrow $I_2$) before being reflected at the interface between the aqueous humor 14 and the lens 16 is not completely canceled by a change in polarization due to birefringence of the cornea 12 in a case where the reflected light passes through the cornea 12 (arrow $I_5$), and the optical rotation due to passing through the cornea 12 is not 0.

This is because an axial angle with respect to the obliquely incident polarized light differs between the incident side and the reflecting side.

In general, an optically active element such as the aqueous humor 14 exerts an optical action of rotating by a retardation around a north pole or south pole of Poincare sphere as a center of the rotation (also referred to as a circular retardation). Since the position of the center of the rotation is fixed, there is no concept of an axis, and light is rotated by the retardation in the same rotation direction regardless of the incident direction or the like.

On the other hand, a birefractive optical element such as the cornea 12 exerts an optical action of rotating by a retardation around an equator of Poincare sphere as a center of the rotation (also referred to as a linear retardation). Which point on the equator is set as the center of the rotation depends on a direction of a slow axis. In the birefractive optical element having an axis as described above, an axis shift occurs depending on the direction in which the light is incident.

Therefore, as described above, in the first step, the optical rotation caused by passing through the aqueous humor 14 is canceled between the incident side and the reflecting side, but the change in polarization caused by passing through the cornea 12 is not canceled between the incident side and the reflecting side.

Therefore, in the polarization state of the first reflected light measured in the first step, the influence of the optical activity of the aqueous humor 14 is negligible, and substantially only the optical characteristics of the cornea 12 can be considered to have affected. Accordingly, the optical characteristics of the cornea 12 can be calculated from information on the polarization state of the first incidence light Sin1 of the first step and information on the polarization state of the first reflected light Sout1.

<Second Step>

Figure 4:
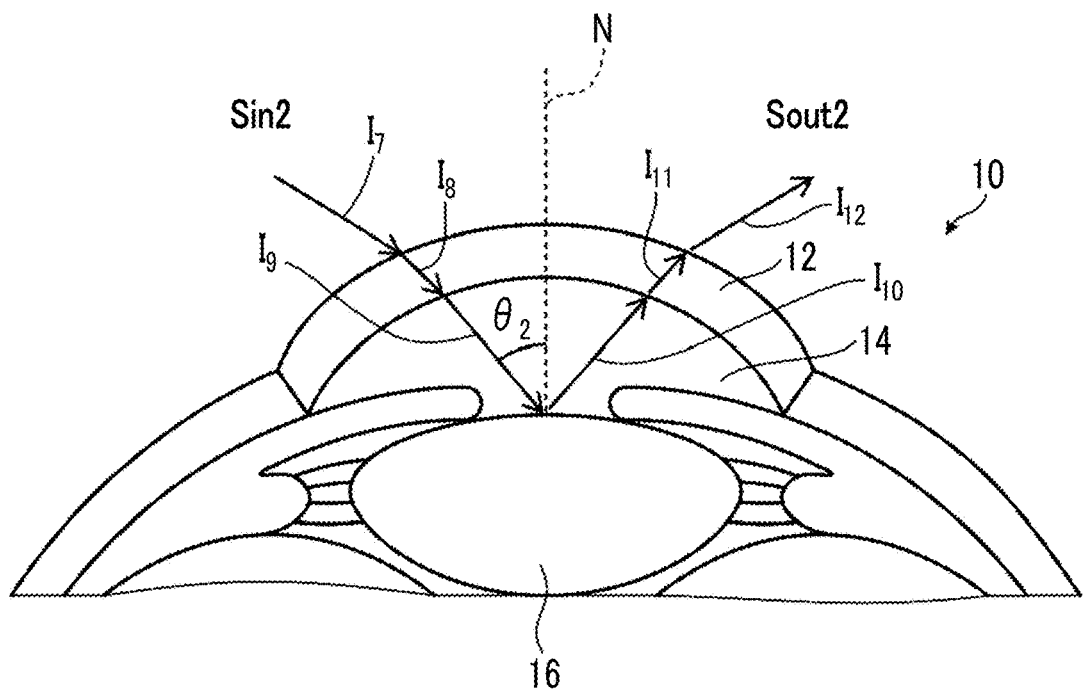
FIG. 4 is a conceptual diagram for explaining a second step of the concentration measuring method of an optically active substance according to the embodiment of the present invention.

Next, the second step will be described with reference to FIG. 4. FIG. 4 shows a conceptual diagram for explaining the second step of the concentration measuring method of an optically active substance according to the embodiment of the present invention.

The second step is a step of measuring, with a measuring unit (not shown), a polarization state a reflected light Sout2, that a second incidence light Sin2 which is polarized is incident from a light source (not shown) toward the aqueous humor 14 of the eye 10 and the reflected light Sout2 is emitted from the eye 10 after being reflected at the interface between the aqueous humor 14 and the lens 16.

Specifically, first, the second incidence light Sin2 emitted from the light source passes through air and is incident on the cornea 12 as indicated by an arrow $I_7$. The light incident on the cornea 12 passes through the cornea 12 and is incident on the aqueous humor 14 as indicated by an arrow $I_8$. The light incident on the aqueous humor 14 reaches the lens 16 through the aqueous humor 14 and is reflected at the interface between the aqueous humor 14 and the lens 16 as indicated by an arrow $I_9$. The reflected light passes through the aqueous humor 14 and is incident on the cornea 12 as indicated by an arrow $I_{10}$. The light incident on the cornea 12 passes through the cornea 12 and is emitted from the eye 10 as indicated by an arrow $I_{11}$. The emitted light (arrow $I_{12}$) is incident on the measuring unit. The measuring unit measures the polarization state of the second reflected light Sout2.

Figure 5:
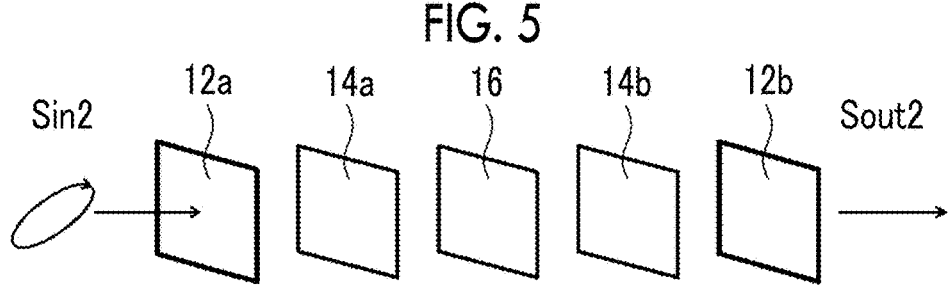
FIG. 5 is a conceptual diagram for explaining a calculation model in the second step.

In such a second step, as the light travels, the polarization state changes due to influence of the cornea 12, the aqueous humor 14, and the reflection. FIG. 5 shows a model for calculating the change in polarization state of light in the second step. FIG. 5 indicates that the second incidence light Sin2 passes through a cornea 12a on the incident side, an aqueous humor 14a on the incident side, the reflection of the lens 16, an aqueous humor 14b on the reflecting side, and a cornea 12b on the reflecting side in this order from the left side of the drawing, and is emitted as the second reflected light Sout2.

In a case where the second incidence light Sin2 passes through the cornea 12a on the incident side, the aqueous humor 14a on the incident side, the aqueous humor 14b on the reflecting side, and the cornea 12b on the reflecting side, is emitted as the second reflected light Sout2 with its polarization plane rotated at each site.

Here, in the second step, an angle $\theta_2$ of the second incidence light Sin2 in a case where the second incidence light Sin2 is reflected at the interface between the aqueous humor 14 and the lens 16 is equal to or larger than the Brewster angle.

In a case where the angle $\theta_2$ of the second incidence light Sin2 is equal to or larger than the Brewster angle, when the second incidence light Sin2 is incident on the interface between the aqueous humor 14 and the lens 16, since the refractive index of the lens is higher than that of the aqueous humor, a phase of s-polarization is shifted by $\pi$ and a phase of p-polarization is also shifted by $\pi$. Therefore, the polarization state of the reflected light does not substantially change.

Therefore, the angle (optical rotation) at which a polarization plane is rotated due to optical activity of the aqueous humor 14 in a case where light passes through the aqueous humor 14 (arrow $I_9$) before being reflected at the interface between the aqueous humor 14 and the lens 16 is not canceled by the optical rotation due to optical activity of the aqueous humor 14 in a case where the reflected light passes through the aqueous humor 14 (arrow $I_{10}$). As a result, the light is affected by the optical activity due to passing the aqueous humor 14.

In addition, the optical rotation due to birefringence of the cornea 12 in a case where light passes through the cornea 12 (arrow $I_8$) before being reflected at the interface between the aqueous humor 14 and the lens 16 is not canceled by the optical rotation due to birefringence of the cornea 12 in a case where the reflected light passes through the cornea 12 (arrow $I_{11}$), and as the light passes through the cornea 12, the light is affected by its optical characteristics.

Therefore, in the polarization state of the second reflected light measured in the second step, the optical activity of the aqueous humor 14 and the optical characteristics (birefringence) of the cornea 12 are affected.

<Third Step>

Next, the third step will be described.

The third step is a step of calculating the optical rotation of the aqueous humor 14 with information on the polarization state of the first reflected light Sout1, which is obtained in the above-described first step, and information on the polarization state of the second reflected light Sout2, which is obtained in the above-described second step.

For example, in the third step, first, information on the optical characteristics of the cornea 12 of the eye 10 is calculated with the information on the first incidence light Sin1 and the information on the polarization state of the first reflected light Sout1, which is obtained in the first step. Next, the optical rotation of the aqueous humor 14 is calculated with the calculated information on the optical characteristics of the cornea, the information on the second incidence light Sin2, and the information on the polarization state of the second reflected light Sout2, which is obtained in the second step.

A method for calculating the optical rotation in the third step will be described in detail later.

<Fourth Step>

Next, the fourth step is a step of calculating a concentration of an optically active substance such as glucose in the aqueous humor 14 from the optical rotation of the aqueous humor 14, which is calculated in the above-described third step.

The aqueous humor has substantially the same components as serum, and contains protein, glucose, ascorbic acid, and the like. It has been known that there is a correlation between a glucose concentration in blood and a glucose concentration in the aqueous humor. Furthermore, a cell substance in the blood does not exist in the aqueous humor, and influence of light scattering is small. The protein, glucose, ascorbic acid, and the like contained in the aqueous humor are optically active substances and have optical activity. Therefore, the aqueous humor is advantageous as a site for optically measuring the concentration of the glucose and the like by utilizing the optical activity. In a case where the concentration of the glucose and the like in the aqueous humor can be optically measured, a blood glucose level can be detected non-invasively.

As a method for calculating the sugar concentration from the optical rotation, various known methods such as a commonly known method using the optical rotation of an aqueous solution of glucose and a correction method using the blood glucose level measured by blood sampling only at the beginning can be used.

As described above, in the method of measuring the glucose concentration by irradiating the aqueous humor in the eye with polarized light and measuring the optical rotation of the polarized light which has passed through the aqueous humor, the polarized light passes through the cornea of the eye as it enters the aqueous humor and as it exits the lens. The cornea has optical characteristics that are more likely to change the polarization than the aqueous humor. Therefore, for example, the optical rotation caused by the aqueous humor cannot be measured accurately, and as a result, there is a problem that measurement accuracy of the glucose concentration in the aqueous humor is low.

On the other hand, in the concentration measuring method of an optically active substance according to the embodiment of the present invention, the first step of measuring the polarization state of first reflected light by irradiating the aqueous humor with the first incidence light such that the angle θ of the incidence light is equal to or smaller than the Brewster angle and the second step of measuring the polarization state of second reflected light by irradiating the aqueous humor with the second incidence light such that the angle θ of the incidence light is equal to or larger than the Brewster angle are included; and the optical rotation due to the aqueous humor is calculated with the information on the polarization state of the first reflected light measured at equal to or smaller than the Brewster angle and the information on the polarization state of the second reflected light measured at equal to or larger than the Brewster angle, and the concentration of the optically active substance in the aqueous humor is calculated from this optical rotation.

As described above, since the influence of the optical activity of the aqueous humor 14 is negligible and substantially only the optical characteristics of the cornea 12 can be considered to have affected, the optical characteristics of the cornea 12 can be calculated from the information on the polarization state of the first reflected light Sout1 measured in the first step. The optical rotation due to the aqueous humor 14 can be calculated with high accuracy from the information on the optical characteristics of the cornea 12 and the information on the polarization state of the second reflected light Sout2 measured in the second step. Therefore, the concentration of the optically active substance in the aqueous humor can be measured with high accuracy.

Hereinafter, the changes in polarization occurring in each of the first step and the second step will be described.

Figure 6:
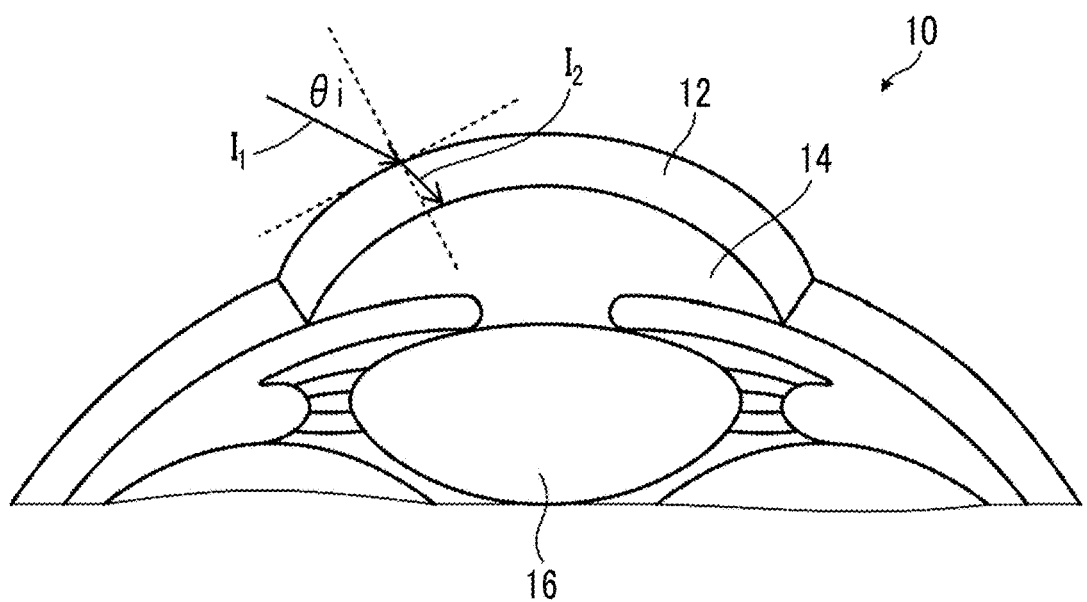
FIG. 6 is a conceptual diagram for explaining a change in polarization between air and cornea.
Figure 7:
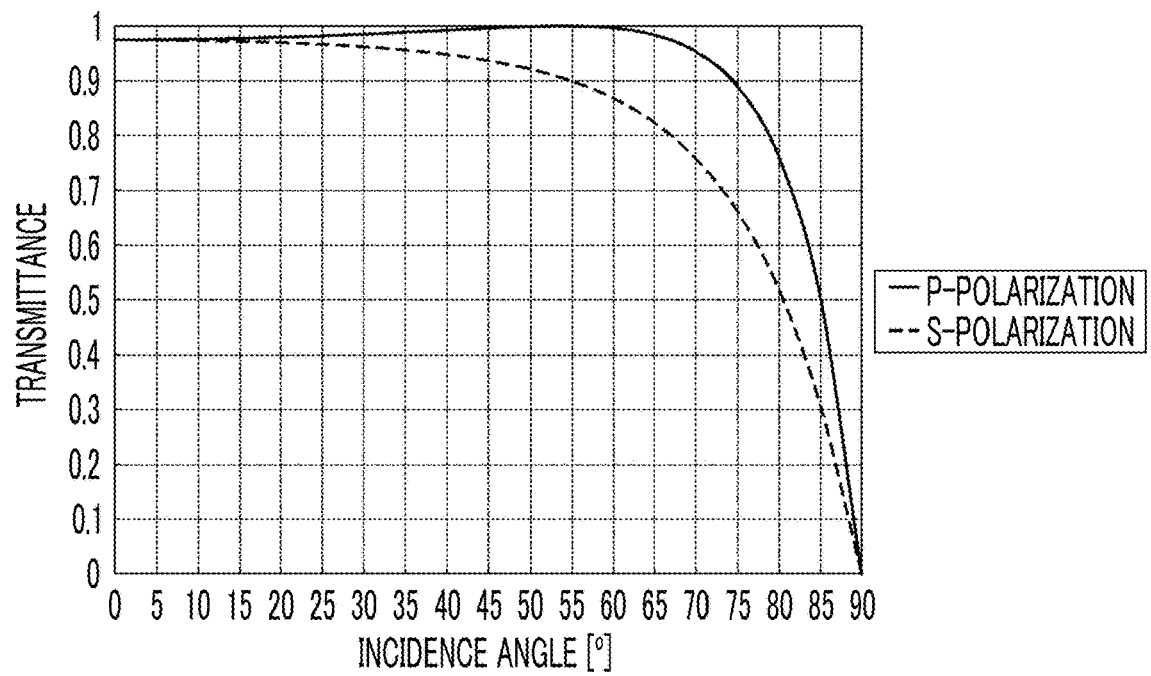
FIG. 7 is a graph showing a change in intensity at an air-cornea interface.

First, in a case where light incident on the cornea 12 from the air (arrow $I_1$), a change in intensity occurs at the interface between the air and the cornea 12 (referred to as a process A). The change in intensity depends on the incidence angle $\theta_i$ (see FIG. 6) on the cornea 12, and different changes occur between the p-polarization and the s-polarization. FIG. 7 shows a graph showing a relationship between the incidence angle $\theta_i$ and transmittance.

The light incident on the cornea 12 from the air travels in the cornea 12 (referred to the arrow $I_2$ and a process B). The cornea 12 has birefringence as an optical characteristic. Therefore, the phase of the light traveling in the cornea 12 changes due to the birefringence of the cornea 12. As described above, the birefringence of the cornea 12 can be calculated from the information on the polarization state of the first reflected light measured in the first step.

Figure 8:
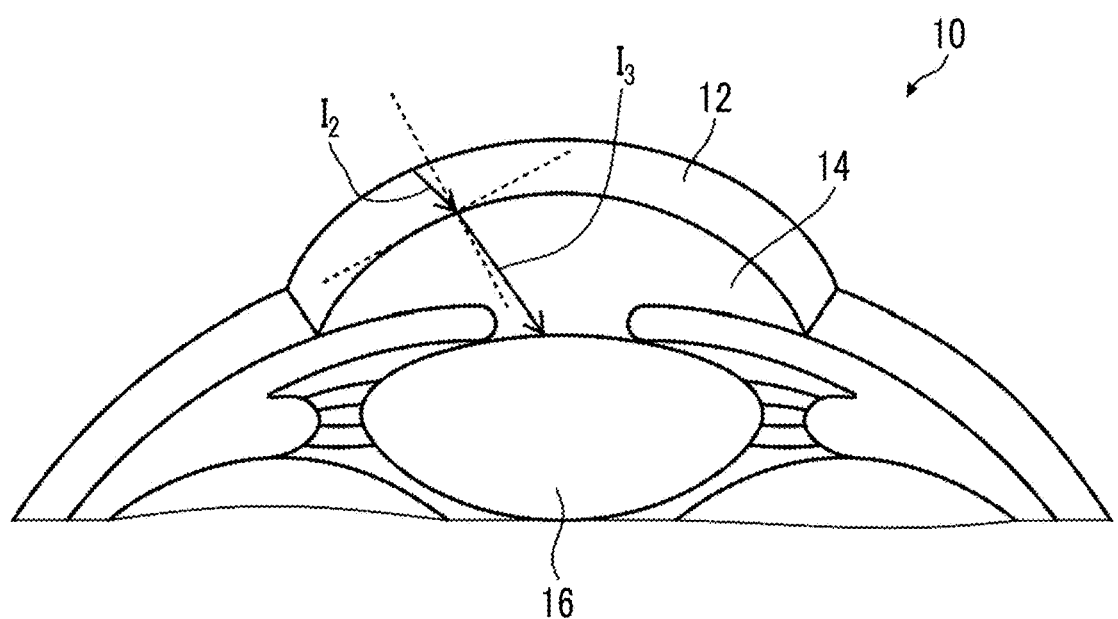
FIG. 8 is a conceptual diagram for explaining a change in polarization between the cornea and aqueous humor.
Figure 9:
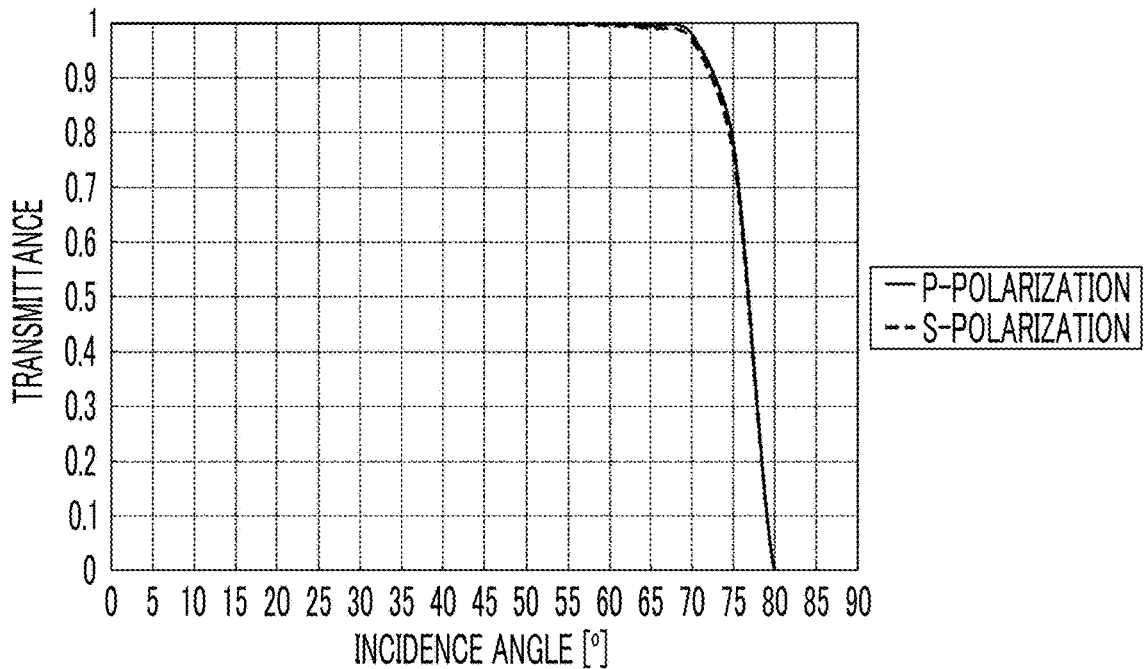
FIG. 9 is a graph showing a change in intensity at a cornea-aqueous humor interface.

Next, as shown in FIG. 8, the light is incident on the aqueous humor 14 from the cornea 12 (referred to as the arrows $I_2$ and $I_3$, and a process C). The refractive indices of the cornea 12 and the aqueous humor 14 are close to each other. Therefore, as shown in the graph in FIG. 9, the change in intensity does not substantially occur in a range in which the incidence angle of light on the interface between the cornea 12 and the aqueous humor 14 is approximately 0° to 65°. In addition, as shown in FIG. 9, there is no difference between the p-polarization and the s-polarization.

The light incident on the aqueous humor 14 from the cornea 12 travels in the aqueous humor 14 (referred to the arrow $I_3$ and a process D). The aqueous humor 14 has optical activity. Therefore, the phase of the light traveling in the aqueous humor 14 changes due to the optical activity of the aqueous humor 14. As described above, the optical activity of the aqueous humor 14 can be calculated from the information on the polarization state of the first reflected light measured in the first step and the information on the polarization state of the second reflected light measured in the second step.

Figure 10:
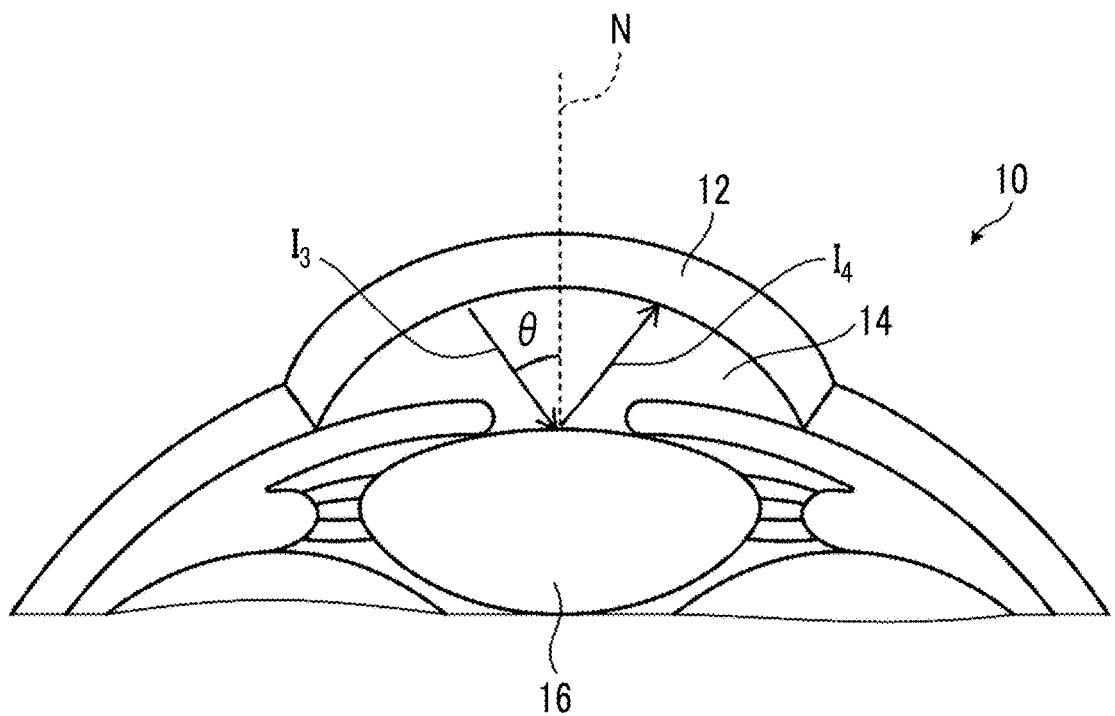
FIG. 10 is a conceptual diagram for explaining a change in polarization between the aqueous humor and lens.

As shown in FIG. 10, the light traveling in the aqueous humor 14 reaches the lens 16, and is reflected at the interface between the aqueous humor 14 and the lens 16 (referred to the arrows $I_3$ and $I_4$, and a process E). Here, as described above, in a case where the angle θ of the light incident on the interface between the aqueous humor 14 and the lens 16 is equal to or smaller than the Brewster angle, since the refractive index of the lens is higher than that of the aqueous humor, a phase of s-polarization is shifted by π and a phase of p-polarization is not shifted. On the other hand, in a case where the angle θ of the light incident on the interface between the aqueous humor 14 and the lens 16 is equal to or larger than the Brewster angle, the phase of s-polarization is shifted by π and the phase of p-polarization is also shifted by π.

The light reflected at the interface between the aqueous humor 14 and the lens 16 travels in the aqueous humor 14 (referred to as the arrow $I_4$ and a process F). As described above, the aqueous humor 14 has optical activity. Therefore, the phase of the light traveling in the aqueous humor 14 changes due to the optical activity of the aqueous humor 14. As described above, in such a first step, in a case where the angle θ of the light reflected at the interface between the aqueous humor 14 and the lens 16 is equal to or smaller than the Brewster angle, the influence of the optical activity received from the aqueous humor 14 before the reflection (arrow $I_3$) and the influence of the optical activity received from the aqueous humor 14 after the reflection (arrow $I_4$) cancel each other out.

In a case where the reflecting surface has a flat shape, the total reflection is performed in a case where the Brewster angle is exceeded, but the reflected light is emitted because the surface (interface) of the lens is curved.

Figure 11:
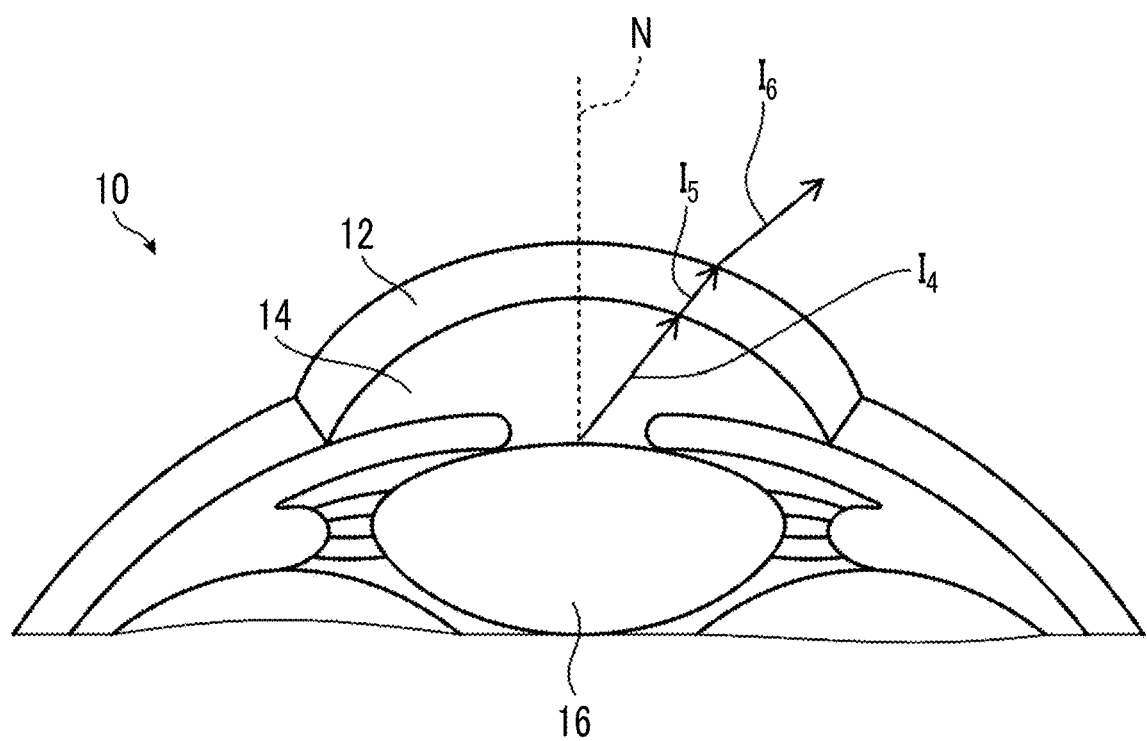
FIG. 11 is a conceptual diagram for explaining a change in polarization in the aqueous humor, the cornea, and the air.

As shown in FIG. 11, the light traveling in the aqueous humor 14 is incident on the cornea 12 from the aqueous humor 14 (referred to as the arrows $I_4$ and $I_5$, and a process G). As described above, since the refractive indices of the cornea 12 and the aqueous humor 14 are close to each other, there is almost no change in intensity.

The light incident on the cornea 12 from the aqueous humor 14 travels in the cornea 12 (referred to as the arrow $I_5$ and a process H). As described above, since the cornea 12 has birefringence as an optical characteristic, the phase of the light traveling in the cornea 12 changes due to the birefringence of the cornea 12.

The light traveling in the cornea 12 is emitted into the air (referred to as the arrows $I_5$ and $I_6$, and a process I). As described above, the change in intensity occurs at the interface between the air and the cornea 12.

By modeling each such process, it can be expressed by an expression of Sout=$M_{IHG} \cdot M_F \cdot M_E \cdot M_D \cdot M_{CBA}$·Sin. Here, Sin is a Stokes vector of the incidence light, Sout is a Stokes vector of the reflected light, M is a Mueller matrix representing each process. That is, $M_{CBA}$ is a Mueller matrix of the processes A to C, $M_D$ is a Mueller matrix of the process D, $M_E$ is a Mueller matrix of the process, $M_F$ is a Mueller matrix of the process F, and $M_{IHG}$ is a Mueller matrix of the processes G to I.

The Mueller matrix is described in [10] S.-Y. Lu and R. A. Chipman "Interpretation of mueller matrices based on polar decomposition", J. Opt. Soc. Am. A, 13, 1996, pp. 1106 to 1113.

In the third step, the optical rotation of the aqueous humor is calculated with such a model expression. Such a model expression will be described below.

First, a Mueller matrix Mref of a change in polarization due to general reflection will be described.

The Mueller matrix Mref of the change in polarization due to reflection can be expressed by the following expression (see, for example, Hiroyuki Fujiwara, spectral ellipsometry, p. 65, Tables 3•2).

$$M_{ref}(\Psi, \Delta) = A \begin{pmatrix} 1 & -\cos2\Psi & 0 & 0 \\ -\cos2\Psi & 1 & 0 & 0 \\ 0 & 0 & \sin2\Psi\cos\Delta & \sin2\Psi\sin\Delta \\ 0 & 0 & -\sin2\Psi\sin\Delta & \sin2\Psi\cos\Delta \end{pmatrix}$$

A, Ψ, and Δ are represented by the following expressions.

$$A = \frac{r_p r_p^* + r_s r_s^*}{2}$$

$$\tan\Psi = \frac{|r_p|}{|r_s|}, \Delta = \delta_{rp} - \delta_{rs}$$

Here, $r_p$ and $r_s$ are amplitude reflection coefficients of the reflected light with respect to a p-wave and an s-wave, respectively, and are derived from Fresnel equation. In addition, $r_p^*$ and $r_s^*$ are complex conjugates thereof (in a case where rp is a real number, $r_p^* = r_p$), δrp and δrs represent the phases of the p-wave and s-wave of the reflected light, respectively, and Δ represents the phase difference.

As described above, the Brewster angle $\theta_B$ is an angle calculated by tan $\theta_B$=nt/ni. In a case where there is no absorption in the medium on the reflecting side and nt>ni, δrp and δrs are expressed by the following relational expressions in a case where the angle of incidence on the medium on the reflecting side is equal to or smaller than the Brewster angle and a case of being equal to or larger than the Brewster angle (see, for example, Hect, Optics I, p. 182, FIGS. 4.44(a) and (b)).

Case of being Less than Brewster Angle:
δrp=0 [deg], δrs=180 [deg], Δ=−180 [deg]
Case of being Brewster Angle or More:
δrp=180 [deg], δrs=180 [deg], Δ=0 [deg]

Next, an expression for expressing the incidence light which is polarized by a combination of natural light, a polarizer, and a phase difference element is described.

In an incident polarized light Spolin, natural light of a light source can be set in various ways by a combination of a polarizer and a phase difference element. That is, assuming that Stokes vectors of the incident polarized light and the natural light are denoted by Spolin and Sin, respectively, Spolin and Sin can be determined from the following expressions. Here, Mpol(θpol) is a Mueller matrix of the polarizer in which a transmission axis is in a θpol direction, and Mret(θret, φ) is a Mueller matrix of the phase difference element having, as the slow axis, a phase difference φ between a slow phase direction and a fast phase direction in a θret direction.

$$S_{polin} = \begin{pmatrix} S_0 \\ S_1 \\ S_2 \\ S_3 \end{pmatrix}, S_{in} = \begin{pmatrix} 1 \\ 0 \\ 0 \\ 0 \end{pmatrix}$$

$$S_{polin} = M_{ret}(\theta_{ret}, \phi) M_{pol}(\theta_{pol}) S_{in}$$

$$M_{pol}(\theta_{pol}) = \frac{1}{2} \begin{pmatrix} 1 & \cos2\theta_{pol} & \sin2\theta_{pol} & 0 \\ \cos2\theta_{pol} & \cos^2 2\theta_{pol} & \sin2\theta_{pol}\cos2\theta_{pol} & 0 \\ \sin2\theta_{pol} & \sin2\theta_{pol}\cos2\theta_{pol} & \sin^2 2\theta_{pol} & 0 \\ 0 & 0 & 0 & 0 \end{pmatrix}$$

$$M_{ret}(\theta_{ret}, \phi) =$$
$$\begin{pmatrix} 1 & 0 & 0 & 0 \\ 0 & \cos^2 2\theta_{ret} + \cos\phi\sin^2 2\theta_{ret} & (1-\cos\phi)\sin2\theta_{ret}\cos2\theta_{ret} & \sin\phi\sin2\theta_{ret} \\ 0 & (1-\cos\phi)\sin2\theta_{ret}\cos2\theta_{ret} & \sin^2 2\theta_{ret} + \cos\phi\cos^2 2\theta_{ret} & -\sin\phi\cos2\theta_{ret} \\ 0 & -\sin\phi\sin2\theta_{ret} & \sin\phi\cos2\theta_{ret} & \cos\phi \end{pmatrix}$$

Next, an expression representing the polarization state of the reflected light measured in the first step and the second step is described below.

As described above, the polarization state of the reflected light measured in the first step and the second step can be expressed by the expression of $S_{out}=M_{IHG} \cdot M_F \cdot M_E \cdot M_D \cdot M_{CBA} \cdot S_{in}$. $S_{in}$ can be expressed by the above-described expression of Spolin. $M_E$ is a Mueller matrix of reflection, and can be expressed by the same expression as Mref described above. $M_{IHG}$ and $M_{CBA}$ are Mueller matrices of the cornea, and can be expressed by the same expression as Mret described above. Hereinafter, $M_{IHG}$ will be referred to as $M_{c2}(\theta_{c2}, \varphi_{c2})$, and $M_{CBA}$ will be referred to as $M_{c1}(\theta_{c1}, \varphi_{c1})$. $M_F$ and $M_D$ are Mueller matrices of the aqueous humor, and can be expressed by the same expression as a Mueller matrix Mrot of an azimuth rotator in which optical activity is $\varepsilon$. Hereinafter, $M_F$ will be referred to as $M_{h2}(\varepsilon_{h2})$, and $M_D$ will be referred to as $M_{h1}(\varepsilon_{h1})$.

$$M_{rot}(\epsilon) = \begin{pmatrix} 1 & 0 & 0 & 0 \\ 0 & \cos 2\epsilon & \sin 2\epsilon & 0 \\ 0 & -\sin 2\epsilon & \cos 2\epsilon & 0 \\ 0 & 0 & 0 & 1 \end{pmatrix}$$

From the above, the polarization state of the reflected light Sout measured in the first step and the second step is represented by the following expression.

$$S_{out}=M_{c2}(\theta_{c2},\varphi_{c2})M_{h2}(\varepsilon_{h2})M_{ref}(\Psi,\Delta)M_{h1}(\varepsilon_{h1})M_{c1}(\theta_{c1},\varphi_{c1})S_{polin} \quad \text{Expression (1)}$$

Next, a method of calculating the optical rotation of the aqueous humor using the above-described expressions in the third step is described below.

The incident polarized light Spolin is known from setting at the time of irradiation of the incidence light, and the reflected polarized light Sout is known from the measurement. On the other hand, the Mueller matrices of the cornea and the aqueous humor of the eye is unknown. In the third step, the Mueller matrices of the cornea and the aqueous humor are obtained using the information on the polarization state of the reflected light measured in the first step and the second step.

As described above, in the first step, polarized light is incident from an air layer such that the angle θ of the incidence light from the aqueous humor to the lens is equal to or smaller than the Brewster angle, and the reflected polarized light is measured. Since optical path lengths of the light passing through the aqueous humor before and after the reflection are substantially the same, $\varepsilon_{h1}$ and $\varepsilon_{h2}$ are substantially the same values, and the phase difference is shifted by 180 degrees by setting the angle θ to be equal to or smaller than the Brewster angle. Therefore, the optical activity $M_{h1}(\varepsilon_{h1})$ by the aqueous humor on the incident side and the optical activity $M_{h2}(\varepsilon_{h2})$ by the aqueous humor on the reflecting side are almost canceled (that is, $M_{h2}(\varepsilon_{h2})$Mref $(\Psi, \Delta)M_{h1}(\varepsilon_{h1})$ is close to the unit matrix). Therefore, the expression (1) described above in the first step can be regarded as the Mueller matrix of the cornea.

In consideration of this, by fitting the relationship between Sout and Spolin by the expression (1) described above, the phase difference and axes ($\theta_{c1}, \varphi_{c1}, \theta_{c2}$, and $\varphi_{c2}$) the cornea can be obtained with high accuracy.

As a fitting method, a minimum square method can be used. In a non-linear minimum square method, unknowns (variables) are applied to a function R(λ) while varying the unknowns (variables) so that the sum of the squares of the difference between the function R(λ) and the normalized amount R of change in polarization state, which is a measured value, is minimized. For this method, an algorithm such as Levenberg-Marquardt method, Quasi-Newton method, and a conjugate gradient method is used.

Next, using the measurement result of the second step of measuring the reflected light so that the angle θ of the incidence light from the aqueous humor to the lens is equal to or larger than the Brewster angle (information on the polarization state of the second reflected light) and the phase difference and axes ($\theta_{c1}, \varphi_{c1}, \theta_{c2}$, and $\varphi_{c2}$) of the cornea, which are obtained as described above, by fitting the relationship between Sout and Spolin by the expression (1) described above, the optical activity of the aqueous humor can be obtained.

In a case where the angle θ is set to be equal to or larger than the Brewster angle, the change in phase disappears, so that the optical activity $M_{h1}(\varepsilon_{h1})$ by the aqueous humor on the incident side and the optical activity $M_{h2}(\varepsilon_{h2})$ by the aqueous humor on the reflecting side are added together, and the optical activity is almost doubled. From the fact and the information on the phase difference and axes (θc1, φc1, θc2, and φc2) of the cornea, the optical activity of the aqueous humor can be obtained with high accuracy.

By measuring at two points of equal to or larger than the Brewster angle and equal to or smaller than the Brewster angle in this way, the birefringence of the cornea and the optical activity of the aqueous humor can be separately calculated, and the optical activity of the aqueous humor can be obtained with high accuracy.

The order in which the first step and the second step are performed is not particularly limited, and the second step may be performed after the first step is performed, or the first step may be performed after the second step is performed. In addition, in the third step, the timing for calculating the optical characteristics of the cornea is also not particularly limited. That is, a part of the third step (step of calculating the optical characteristics of the cornea) may be performed before the second step is performed, and then the remaining step of the third step (step of calculating the optical rotation of the aqueous humor) may be performed after the second step is performed.

Here, it is preferable that the first step is performed a plurality of times under conditions in which the angle $\theta_1$ between the normal line to the tangent plane at a point where the first incidence light intersects the surface of the lens and the first incidence light is different, so that a plurality of pieces of the information on the polarization state of the first reflected light in the first step are acquired, and the third step is performed with the plurality of pieces of the information acquired.

By performing the first step a plurality of times under different conditions of the angle $\theta_1$ and calculating the optical characteristics of the cornea by fitting using a plurality of pieces of the information on the polarization state of the reflected light, optical information on the cornea can be obtained with higher accuracy.

In addition, as described above, from the results of the first step, the optical characteristics (birefringence) of the cornea can be calculated. Here, the phase difference of the cornea obtained by the expression (1) described above corresponds to an in-plane retardation Re viewed from the incidence direction of light, but the cornea also has a thickness direction retardation Rth. The thickness direction retardation Rth cannot be calculated from one measurement, but by performing the first step a plurality of times under different conditions of the angle $\theta_1$ to acquire a plurality of pieces of information on the polarization state of the first reflected light, and setting up a plurality of the expressions (1) described above using the polarization state of each first reflected light and performing fitting, the in-plane retardation Re and the thickness direction retardation Rth of the cornea can be calculated.

In addition, it is preferable that the second step is performed a plurality of times under conditions in which the angle $\theta_2$ between the normal line to the tangent plane at a point where the second incidence light intersects the surface of the lens and the second incidence light is different, so that a plurality of pieces of the information on the polarization state of the second reflected light in the second step are acquired, and the third step is performed with the plurality of pieces of the information acquired.

By performing the second step a plurality of times under different conditions of the angle $\theta_2$ and calculating the optical activity of the aqueous humor by fitting using a plurality of pieces of the information on the polarization state of the reflected light, the optical activity of the aqueous humor can be obtained with higher accuracy.

In addition, it is preferable that the first step is performed a plurality of times while changing a wavelength of the first incidence light, so that a plurality of pieces of the information on the polarization state of the first reflected light in the first step are acquired, and the third step is performed with the plurality of pieces of the information acquired.

In addition, it is preferable that the second step is performed a plurality of times while changing a wavelength of the second incidence light, so that a plurality of pieces of the information on the polarization state of the second reflected light in the second step are acquired, and the third step is performed with the plurality of pieces of the information acquired.

It is known that albumin and ascorbic acid are contained in the aqueous humor as a component having optical activity, in addition to the glucose. Here, a wavelength dependence of the optical rotation by the optically active substance differs depending on the type of the optically active substance. Therefore, by performing the first step and/or the second step a plurality of times while changing the wavelength of the incidence light to acquire a plurality of pieces of information on the polarization state of the reflected light, based on the wavelength dependence of each optically active substance, a proportion of the glucose in the aqueous humor can be determined.

Specifically, in an object to be measured, which contains a single optically active substance, the optical rotation $\varphi$ with respect to a wavelength $\lambda$ is represented by the product of an optical path length L and a concentration C. The optical rotation $\varphi$ is represented by a Drude monomial expression that is a non-linear function in which a monotonic decrease or a monotonous increase occurs in a wavelength region longer than the local maximum point and/or the local minimum point. The Drude monomial expression is an example of a function representing a rotational dispersion of the optically active substance. In a case where the object to be measured contains a plurality of optically active substances, the optical rotation $\varphi$ is described by the addition of optical rotations $\varphi_j$ of each optically active substance represented by the Drude monomial expression. In other words, the observed optical rotation $\varphi$ is represented by the sum of functions representing the wavelength dependence of the optical rotations $\varphi_j$ of each optically active substance. j is an integer of 1 or more.

As an example, it is assumed that the optical rotation $\varphi_{AH}$ due to the aqueous humor is represented by the sum of two Drude monomial expressions represented by the following expression (2). The first term on the right side is a term in which the glucose contributes in a case where the glucose is an optically active substance to be obtained. The second term on the right side is a term in which other optically active substances other than the glucose contribute. The concentration of glucose is denoted by a glucose concentration $C_g$. $A_g$ and $\lambda_g$ are constants specific to the optically active substance (glucose) (eigenvalues which define the characteristics of the rotational dispersion of the optically active substance (glucose)). $A_x$ and $\lambda_x$ are eigenvalues in a case where other optically active substances are added together. In addition, L is the optical path length. Therefore, the optical rotation $\varphi_{AH}$ due to the aqueous humor is expressed as a function of $A_x$ and $\lambda_x$, which are eigenvalues in a case where the glucose concentration $C_g$ and other optically active substances are combined.

$$\phi_{AH}(C_g, A_x, \lambda_x) = L \cdot \left( \frac{A_g}{\lambda^2 - \lambda_g^2} \cdot C_g + \frac{A_x}{\lambda^2 - \lambda_x^2} \right) \qquad \text{Expression (2)}$$

In the expression (2), although the optically active substances other than the glucose contained in the aqueous humor are summarized, they may be represented by a plurality of terms for the other optically active substances. For example, in addition to the term of the glucose, a term of albumin, globulin, or the like may be provided. In this case, any optically active substance other than the optically active substance (glucose, albumin, globulin, and the like) having the term may be treated as a term of the other optically active substances. Furthermore, in a case where the contribution of the other optically active substances is small, it is not necessary to provide the term of the other optically active substances. That is, the term may be set in consideration of a degree of influence on the optical rotation $\Phi_{AH}$ by the desired optically active substance and the aqueous humor, and the like.

By using the expression (2) described above after performing the first step and/or the second step a plurality of times while changing the wavelength of the incidence light to acquire a plurality of pieces of information on the polarization state of the reflected light, and obtaining the optical rotation of the aqueous humor for each wavelength using the expression (1) described above, the concentration of the glucose in the aqueous humor can be determined more accurately.

In the present invention, the optically active substance for which the concentration is measured is preferably glucose.

In addition, it is more preferable to perform the first step and the second step with incidence light having different wavelengths. By performing the first step and the second step for each wavelength, calculating a wavelength dispersion of the optical activity (referred to as $\Phi$measure) of the entire aqueous humor from these, and determining a mixing ratio such that $\Phi$ in the expression (2) described above matches $\Phi$measure, the concentration of the glucose in the aqueous humor can be determined more accurately.

In addition, in the first step, the angle $\theta_1$ between the normal line to the tangent plane at a point where the first incidence light intersects the surface of the lens and the first incidence light is not particularly limited as long as it is equal to or smaller than the Brewster angle, but it is preferably 2° to 45°, more preferably 3° to 35°, and still more preferably 4° to 25°.

In addition, in the second step, the angle $\theta_2$ between the normal line to the tangent plane at a point where the second incidence light intersects the surface of the lens and the second incidence light is not particularly limited as long as it is equal to or larger than the Brewster angle, but it is preferably more than the Brewster angle, more preferably 50° to 65°, and still more preferably 50 to 60°.

[Concentration Measuring Device of Optically Active Substance]

The concentration measuring device of an optically active substance according to the embodiment of the present invention is a concentration measuring device of an optically active substance, which is for performing the above-described concentration measuring method of an optically active substance, the concentration measuring device including:

a light source for irradiating an incidence light which is polarized to an aqueous humor in an eye;

a measuring unit for measuring a polarization state of a reflected light obtained by reflecting the incidence light at an interface between the aqueous humor and a lens;

a control unit for controlling an incidence angle of the incidence light; and a calculation unit for calculating an optical rotation of the aqueous humor using information on the polarization state of the reflected light, which is measured by the measuring unit.

Figure 12:
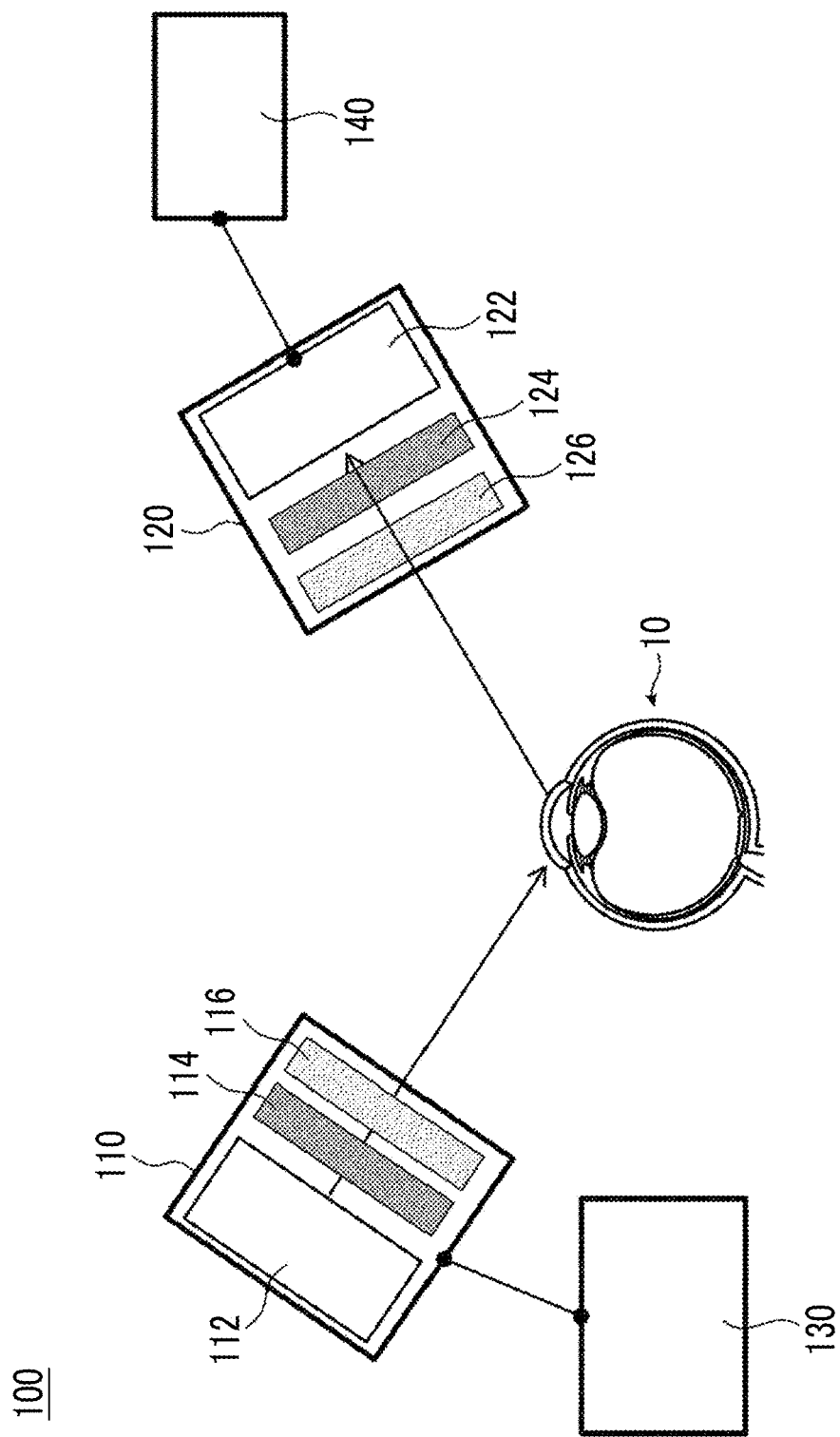
FIG. 12 is a diagram conceptually showing an example of a concentration measuring device of an optically active substance according to the embodiment of the present invention.

FIG. 12 is a diagram conceptually showing an example of the concentration measuring device of an optically active substance.

The concentration measuring device 100 of an optically active substance shown in FIG. 12 includes a light source 110, a measuring unit 120, a control unit 130, and a calculation unit 140.

<Light Source>

The light source 110 irradiates a polarized light to the aqueous humor of the eye 10.

In the example shown in FIG. 12, as an example, the light source 110 has a light emitting element 112, a polarizing plate 114 which converts light emitted from the light emitting element 112 into the polarized light, and a phase difference plate 116 which converts a polarization state of the polarized light converted by the polarizing plate 114. Since the light source 110 has the polarizing plate 114 and the phase difference plate 116, light in a desired polarization state can be emitted.

The configuration of the light source 110 is not limited to this. For example, the light emitting element 112 and the polarizing plate 114 may be provided, only the light emitting element 112 which emits the polarized light may be provided, or the light emitting element 112 and the phase difference plate 116 may be provided.

(Light Emitting Element)

Examples of the light emitting element 112 include a light bulb such as a mercury lamp, a fluorescent lamp, a halogen lamp, a light emitting diode (LED), and a laser such as a semiconductor laser. As the light emitting element 112, it is preferable to use an LED capable of irradiating light in a narrow band, or a laser such as a semiconductor laser.

The wavelength of the light emitted by the light emitting element 112 is also not limited, and may be visible light or invisible light such as infrared rays and ultraviolet rays. Among these, visible light or near infrared rays are suitably used as the light emitted by the light emitting element 112.

Furthermore, the light emitted by the light emitting element 112 may be unpolarized or polarized. In a case where the light emitting element 112 emits polarized light, the emitted light may be linearly polarized light or circularly polarized light.

(Polarizing Plate)

The polarizing plate is not particularly limited, and various known polarizing plates can be appropriately used.

An iodine-based polarizer, a dye-based polarizer using a dichroic dye, a polyene-based polarizer, or the like, which is an absorption type polarizer, is used as an absorptive type linearly polarizing plate. The iodine-based polarizer and the dye-based polarizer include a coating-type polarizer and a stretching-type polarizer, and any of these is applicable. Among these, a polarizer produced by adsorbing iodine or a dichroic dye on polyvinyl alcohol and stretching the resultant is preferable.

In addition, examples of a method of obtaining a polarizer by performing stretching and dyeing in a state of a laminated film in which a polyvinyl alcohol layer is formed on a substrate include methods disclosed in JP5048120B, JP5143918B, JP4691205B, JP4751481B, and JP4751486B, and known technologies related to these polarizers can be preferably used.

As the absorption type polarizer, a polarizer in which the dichroic coloring agent is aligned using aligning properties of liquid crystal without stretching is particularly preferable. The above-described polarizer has many advantages such as that it is possible to form a very thin layer having a thickness of approximately 0.1 μm to 5 μm, it is difficult to occur cracks or thermal deformation in a case of being bent as described in JP2019-194685A, excellent durability is obtained even for a polarizing plate having a high transmittance of more than 50% as described in JP6483486B, heat moldability is excellent, and the like. In addition, it is also possible to peel off a support and transfer the polarizer for use.

As a reflective type linearly polarizing plate, a film obtained by stretching a layer including two types of polymers, a wire grid polarizer, or the like as described in JP2011-053705A can be used. From the viewpoint of brightness, a film in which a layer including a polymer is stretched is preferable. As a commercially available product thereof, a reflective type polarizer (trade name: APF) manufactured by 3M Company, a wire grid polarizer (trade name: WGF) manufactured by Asahi Kasei Corporation, or the like can be suitably used.

(Phase Difference Plate)

The phase difference plate is a phase difference plate which converts the phase of the incident polarized light. The phase difference plate is disposed by adjusting a direction of the slow axis with respect to a transmission axis of the polarizing plate, so that the polarized light emitted from the light source 110 is in a desired polarization state.

The phase difference plate used in the present invention may be a single-layer type composed of one optically anisotropic layer, or may be a multi-layer type composed of a lamination of two or more optically anisotropic layers each having a plurality of different slow axes. Examples of the multi-layer type phase difference plate include WO2013/137464A, WO2016/158300A, JP2014-209219A, JP2014-209220A, WO2014/157079A, JP2019-215416A, and WO2019/160044A, but the multi-layer type phase difference plate is not limited thereto.

<Control Unit>

The control unit 130 is a portion which controls the direction and position of the light source 110 to irradiate the light, and adjusts the light emitted by the light source 110 to be emitted toward the position where the eyes of the subject are arranged.

It is sufficient that the control unit 130 has a mechanism for moving the position of the light source 110, a mechanism for rotating the light source 110, and the like. As such a mechanism, a known mechanism can be appropriately used.

Specifically, in order to change the incidence angle of the light incident on the eyes, the control unit 130 changes the position and the angle of the light source 110 such that a polar angle is changed with the position of the eyes as the origin.

In addition, the control unit 130 may have a rotation mechanism which rotates the polarizing plate 114 of the light source 110 about an axis perpendicular to the main surface of the polarizing plate 114.

In addition, the control unit 130 may have a rotation mechanism which rotates the phase difference plate 116 of the light source 110 about an axis perpendicular to the main surface of the phase difference plate 116.

By having the rotation mechanism which rotates the polarizing plate 114 and/or the phase difference plate 116, it is possible to change the polarization state of the polarized light emitted from the light source 110.

<Measuring Unit>

The measuring unit 120 is a portion which measures the polarization state by receiving the reflected light obtained by the irradiation from the light source 110 and reflecting the light at the interface between the aqueous humor and the lens. As the measuring unit 120, various known measuring devices can be used as long as it can detect the polarization state of the received light.

In the example shown in FIG. 12, as an example, the measuring unit 120 has a light receiving element 122, a polarizing plate 124, and a phase difference plate 126.

Figure 19:
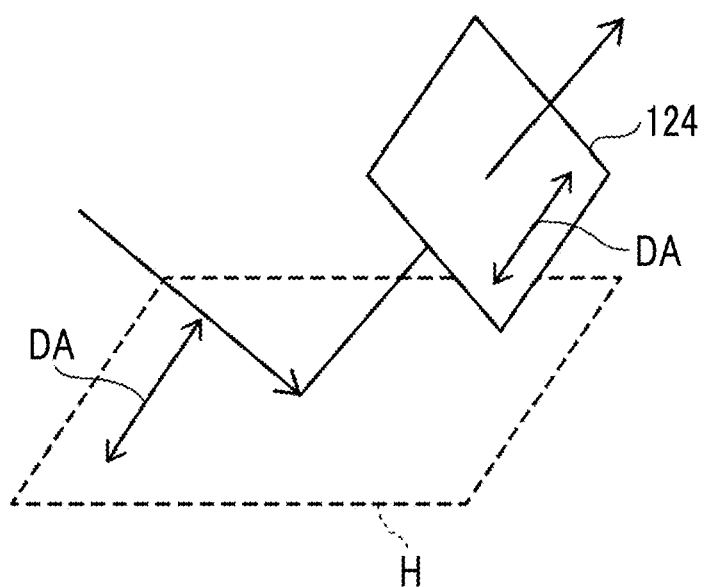
FIG. 19 is a perspective view illustrating a disposure of a polarizing plate in the measuring unit.
Figure 20:
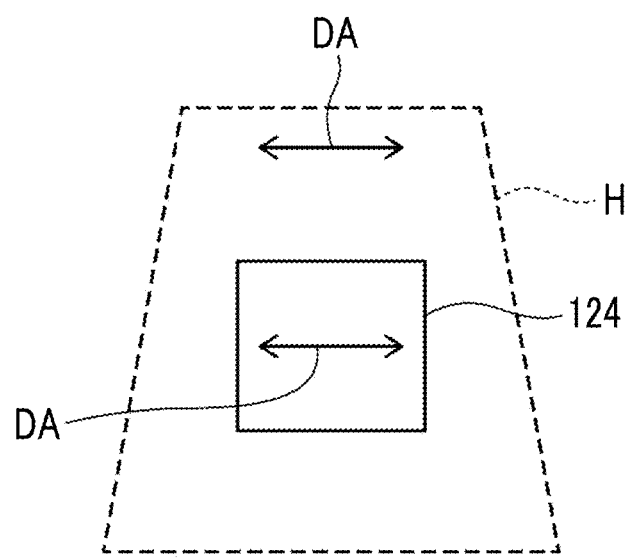
FIG. 20 is a view of FIG. 19 as viewed from another direction.

Such a measuring unit can measure the polarization state of the reflected light by the same principle as that of a rotation compensator type ellipsometry. In this case, in principle, the phase difference plate 126 may be rotated. In addition, as the phase difference plate 126, a $\lambda/4$ plate which is $\lambda/4$ with respect to the wavelength $\lambda$ of the incidence light may be used. In addition, as shown in FIGS. 19 and 20, in a case where a horizontal direction DA of the tangent plane H viewed from the main surface of the polarizing plate 124 is defined as 0°, the polarizing plate 124 may be disposed such that the transmission axis is 45° or 135°.

In order to receive the reflected light, the measuring unit 120 is controlled in the direction, the position, and the like by a control unit (not shown). Specifically, the position and the angle of the measuring unit 120 are changed such that the polar angle is changed with the position of the eyes as the origin, so that the reflected light is incident on the measuring unit 120 perpendicularly. In addition, the measuring unit 120 may be controlled in the direction, position, and the like in conjunction with the control of the direction and the position of the light source 110 by the control unit 130.

Hereinafter, an example of the measuring unit will be described.

Figure 13:
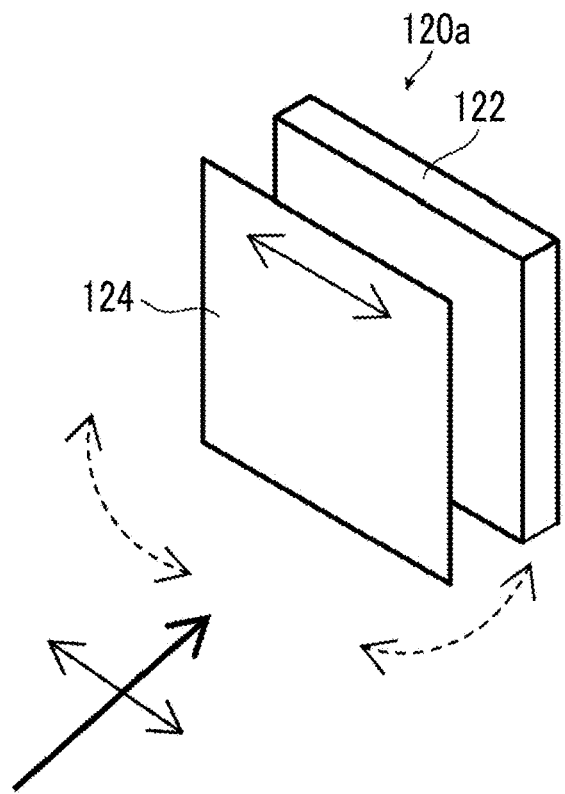
FIG. 13 is a schematic diagram for explaining another example of a measuring unit.

FIG. 13 is a diagram conceptually showing an example of the measuring unit.

A measuring unit 120a shown in FIG. 13 has a light receiving element 122 and a polarizing plate 124.

Figure 14:
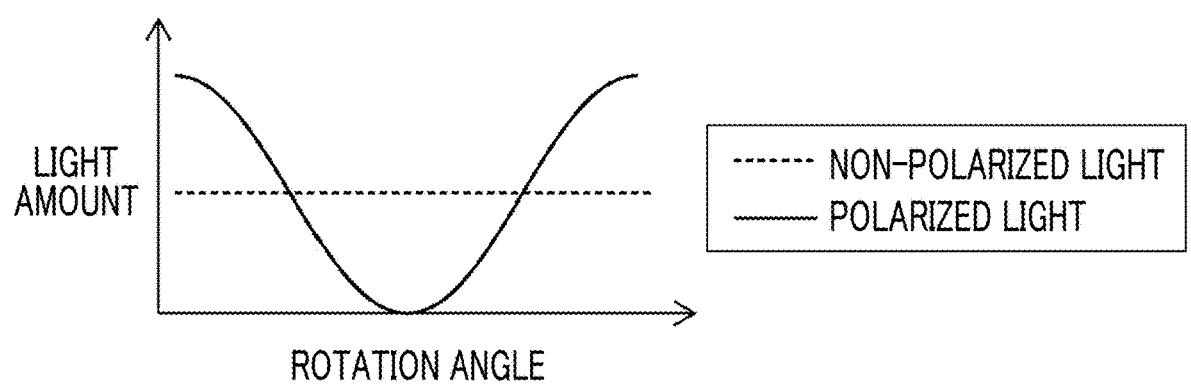
FIG. 14 is a graph showing a relationship between a rotation angle and a light amount.

In the measuring unit 120a shown in FIG. 13, the polarizing plate 124 is rotated about an axis perpendicular to the main surface of the polarizing plate 124, and the light receiving element 122 receives the reflected light which has passed through the polarizing plate 124. For example, in a case where the light incident on the measuring unit 120a is linearly polarized light, and a case where the transmission axis of the polarizing plate 124 and a vibration direction of the linearly polarized light are the same, the linearly polarized light is almost transmitted and received by the light receiving element 122, so that the light receiving element 122 detects light with a high light amount (intensity). On the other hand, in a case where the transmission axis of the polarizing plate 124 and the vibration direction of the linearly polarized light are orthogonal to each other, the linearly polarized light is mostly shielded, so that the light receiving element 122 detects light with a weak light amount (intensity). Therefore, by rotating the polarizing plate 124, as shown in FIG. 14, the light amount (intensity) detected by the light receiving element 122 changes according to a rotation angle of the polarizing plate. Accordingly, it is possible to detect the polarization state of the light incident on the measuring unit 120a from the change in light amount.

(Light Receiving Element)

The light receiving element 122 is a known photodetector such as a silicon diode, and outputs an electric signal corresponding to the intensity of the incident light.

Figure 15:
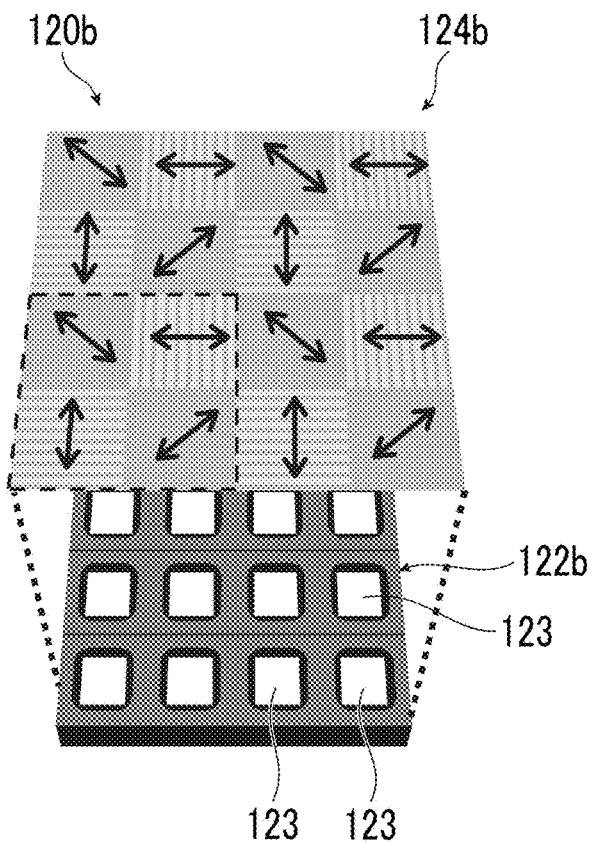
FIG. 15 is a schematic diagram for explaining another example of the measuring unit.

FIG. 15 is a diagram conceptually showing another example of the measuring unit.

A measuring unit 120b shown in FIG. 15 has a light receiving element 122b and a polarizing plate 124b.

(Two-Dimensional Sensor)

The light receiving element 122b is a two-dimensional sensor in which light receiving sections 123 for receiving light are two-dimensionally arranged in one plane direction and in a direction orthogonal to this one direction. Each of the light receiving sections 123 outputs an electric signal corresponding to the intensity of the incident light. As the two-dimensional sensor, a known image sensor such as a complementary MOS (CMOS) and a charge coupled device (CCD) can be used. In addition, the two-dimensional sensor may be configured by two-dimensionally arranging known photodetectors such as a silicon diode as the light receiving sections 123.

(Patterned Polarizing Plate)

In the polarizing plate 124b, regions in which directions of the transmission axes are different from each other are arranged in a predetermined pattern (hereinafter, also referred to as a patterned polarizing plate). In the example shown in FIG. 15, four regions having different directions of the transmission axes are regarded as one set, and a plurality of these sets are arranged two-dimensionally. In addition, the patterned polarizing plate 124b is disposed such that each region corresponds to each light receiving section 123 of the two-dimensional sensor 122b.

As an example, in FIG. 15, a first region in which the direction of the transmission axis is a vertical direction, a second region which is disposed on the right side of the first region and in which the direction of the transmission axis extends from the upper right to the lower left, a third region which is disposed on the upper side of the second region and in which the direction of the transmission axis is a left-right direction, and a fourth region which is disposed on the left side of the third region and in which the direction of the transmission axis extends from the upper left to the lower right are regarded as one set, and a plurality of these sets are provided.

The operation of the measuring unit 120b having such a two-dimensional sensor 122b and a patterned polarizing plate 124b will be described with reference to FIG. 16.

Figure 16:
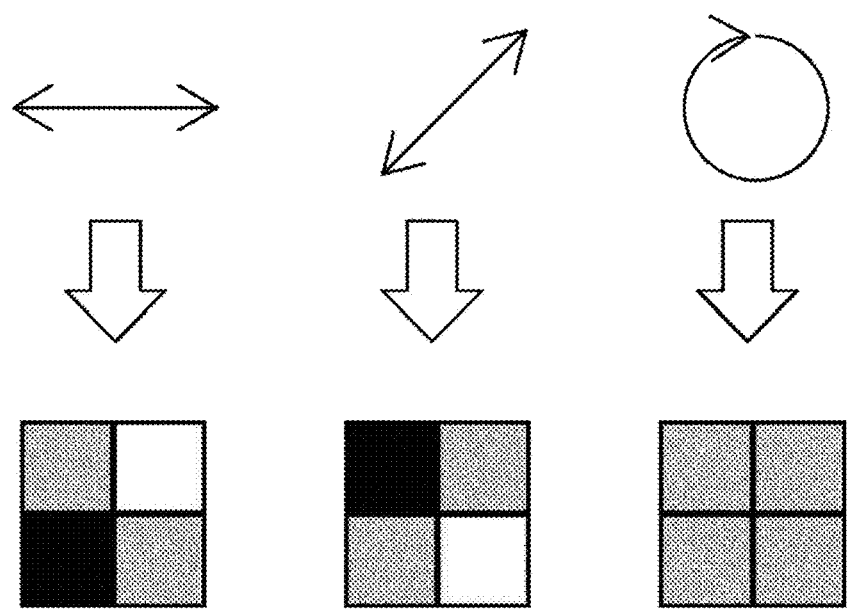
FIG. 16 is a diagram showing a relationship between a polarization state and a light receiving pattern.

As shown in the diagram on the left side of FIG. 16, in a case where linearly polarized light vibrating in the left-right direction is incident on the measuring unit 120b, in the first region of the patterned polarizing plate 124b, since the direction of the transmission axis and the vibration direction of the linearly polarized light are perpendicular to each other, the light is almost shielded. Therefore, the light amount is hardly detected in the light receiving section corresponding to the first region. In the second region and the fourth region, since the direction of the transmission axis and the vibration direction of the linearly polarized light are approximately 45°, a part of the linearly polarized light is transmitted. Therefore, an intermediate light amount is detected in the light receiving sections corresponding to the second region and the fourth region. In the third region, since the direction of the transmission axis and the vibration direction of the linearly polarized light are parallel to each other, the linearly polarized light is almost transmitted. Therefore, a high light amount is detected in the light receiving section corresponding to the third region.

That is, as shown in the diagram on the lower left side of FIG. 16, different light amounts are detected in the light receiving sections corresponding to the first to fourth regions. In the figure, a case where the light amount detected by the light receiving section is high is represented by white, a case where the light amount detected is middle is represented by gray, and a case where the light amount detected is low is represented by black.

On the other hand, as shown in the diagram on the left-right middle side of FIG. 16, in a case where the linearly polarized light vibrating from the upper right to the lower left is incident, in the first region and the third region of the patterned polarizing plate 124b, since the direction of the transmission axis and the vibration direction of the linearly polarized light are at approximately 45°, a part of the linearly polarized light is transmitted. Therefore, an intermediate light amount is detected in the light receiving sections corresponding to the first region and the third region. In the second region, since the direction of the transmission axis and the vibration direction of the linearly polarized light are parallel to each other, the linearly polarized light is almost transmitted. Therefore, a high light amount is detected in the light receiving section corresponding to the second region. In the fourth region, since the direction of the transmission axis and the vibration direction of the linearly polarized light are orthogonal to each other, the linearly polarized light is almost shielded. Therefore, the light amount is hardly detected in the light receiving section corresponding to the fourth region.

That is, as shown in the diagram on the lower center side of FIG. 16, different light amounts are detected in the light receiving sections corresponding to the first to fourth regions. In addition, as shown in FIG. 16, a pattern of the light amount detected is different from that of linearly polarized light vibrating in the left-right direction (lower left diagram in FIG. 16).

As described above, in the measuring unit 120b, the two-dimensional sensor 122b detects different light amount patterns depending on the direction of the incident linearly polarized light. Therefore, it is possible to detect the polarization state of the received polarized light from the light amount patterns detected by the two-dimensional sensor 122b.

In the example shown in FIG. 15, the patterned polarizing plate 124b is configured to have four types of regions in which the directions of the transmission axes are different, but the patterned polarizing plate 124b is not limited to this, and may have a plurality of types of regions in which the directions of the transmission axes are different. For example, the configuration may include nine types of regions in which the directions of the transmission axes are different.

Figure 17:
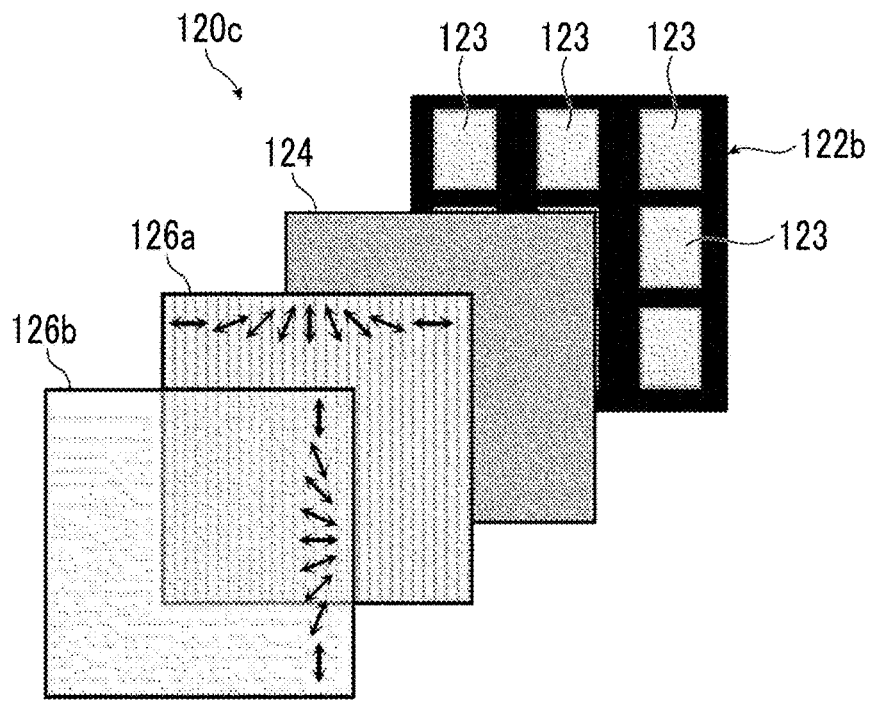
FIG. 17 is a schematic diagram for explaining another example of the measuring unit.

FIG. 17 is a diagram conceptually showing another example of the measuring unit.

A measuring unit 120c shown in FIG. 17 has a light receiving element 122b, a polarizing plate 124, a first phase difference plate 126a, and a second phase difference plate 126b.

Each of the first phase difference plate 126a and the second phase difference plate 126b has a patterned optically anisotropic layer. The patterned optically anisotropic layer has a plurality of unit each composed of a plurality of band-like regions, in which the phase difference is constant, the unit is divided into the plurality of band-like regions in the same plane, the direction of the slow axis in one band-like region is the same, and the directions of the slow axes in each band-like region is all different from each other.

In addition, the band-like region of the patterned optically anisotropic layer of the first phase difference plate 126a and the band-like region of the patterned optically anisotropic layer of the second phase difference plate 126b are arranged to intersect each other in the plane direction.

In addition, the first phase difference plate 126a and the second phase difference plate 126b are different phase difference plates, and for example, one is a $\lambda/4$ plate and the other is a $\lambda/2$ plate.

The patterned optically anisotropic layers of the first phase difference plate 126a and the second phase difference plate 126b are formed by a liquid crystal composition containing a liquid crystalline compound and aligning the liquid crystalline compound in a predetermined alignment pattern.

The measuring unit 120c having such a first phase difference plate 126a and a second phase difference plate 126b can perform a measurement by distinguishing the polarization state of the incident light. A measuring unit having such a configuration is described in detail in JP6616494B.

Here, in the measuring unit 120b shown in FIG. 15, in a case where a circularly polarized light is incident, as shown in the diagram on the right side of FIG. 16, since approximately the same light amount is detected by the light receiving sections corresponding to the first to fourth regions, a dextrorotatory circularly polarized light and a levorotatory circularly polarized light cannot be distinguished. In addition, an unpolarized light cannot be distinguished. On the other hand, the measuring unit 120c shown in FIG. 17 can distinguish not only the linearly polarized light but also the circularly polarized light.

In addition, in the case of the measuring unit 120b shown in FIG. 15, there is a problem that the positions of the regions of the patterned polarizing plate 124b and the light receiving sections of the two-dimensional sensor 122b are likely to be dislocated. On the other hand, in the measuring unit 120c shown in FIG. 17, since only the first phase difference plate 126a and the second phase difference plate 126b are arranged, the dislocation does not occur, so that the polarization state of the received light can be detected with higher accuracy.

Figure 18:
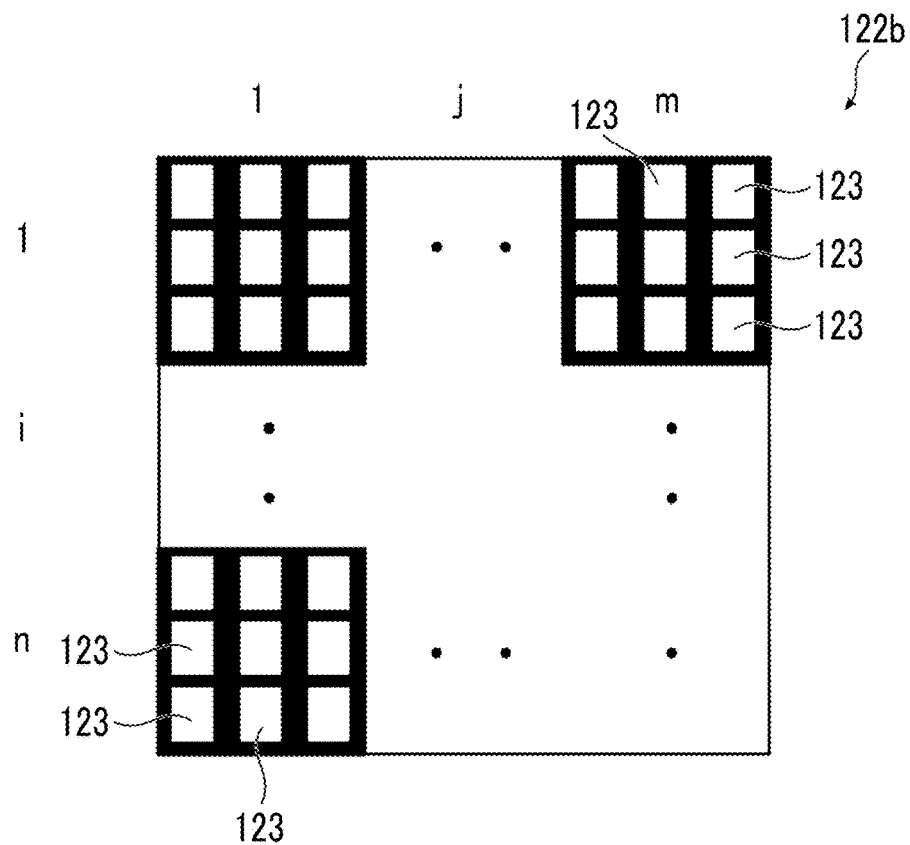
FIG. 18 is a schematic diagram for explaining another example of a light receiving element.

In addition, it is preferable that the two-dimensional sensor 122b in the measuring unit 120b shown in FIG. 15 and in the measuring unit 120c shown in FIG. 17 has a plurality of sets of a plurality of light receiving sections 123, and each set detects the polarization state of light. For example, an example shown in FIG. 18 has n×m sets of 3×3 light receiving sections 123. By using such a two-dimensional sensor 122b, a plurality of polarization states can be detected. By detecting the polarization state in a plurality of sets, calculating the optical rotation of the aqueous humor for each set, and averaging the optical rotation, the accuracy of the optical rotation to be obtained can be higher.

In addition, the measuring unit may perform the measurement of the polarization state a plurality of times. By performing the measurement a plurality of times, detecting the polarization state a plurality of times, calculating the optical rotation of the aqueous humor from each detection result, and averaging the optical rotation, the accuracy of the optical rotation to be obtained can be higher.

In addition, the optical rotation may be obtained by performing the measurement with a plurality of sets of light receiving sections and performing the measurement a plurality of times, calculating the optical rotation of the aqueous humor from each detection result, and averaging the optical rotation.

<Calculation Unit>

The calculation unit 140 is a portion which calculates the optical rotation of the aqueous humor with the information on the polarization state of the incidence light emitted from the light source 110, the information on the polarization state of the reflected light measured in the measuring unit 120, and the like. That is, the calculation unit 140 performs the third step of the above-described concentration measuring method of an optically active substance to calculate the optical rotation of the aqueous humor. In addition, the calculation unit 140 may perform the fourth step to calculate the concentration of the optically active substance from the optical rotation of the aqueous humor.

The calculation unit 140 is configured as a computer having an arithmetic processing unit such as a central processing unit (CPU) and a graphics processing unit (GPU), a memory such as a random access memory (RAM) and a read only memory (ROM), a storage medium such as a hard disk drive (HDD) and a solid state drive (SSD), and the like. A program for calculating the optical rotation of the aqueous humor and/or a program for calculating the concentration of the optically active substance are stored in the ROM or the storage medium.

In the concentration measuring device 100 of an optically active substance, the information on the optical rotation of the aqueous humor calculated by the calculation unit 140 and/or the information on the concentration of the optically active substance may be displayed on a monitor (not shown) or transmitted to another device such as a smartphone.

In addition, in the example shown in FIG. 12, the light source 110 has the light emitting element 112, the polarizing plate 114, and the phase difference plate 116, and the measuring unit 120 has the phase difference plate 126, the polarizing plate 124, and the light receiving element 122, but the configuration thereof is not limited thereto.

For example, the configuration may be that the light source 110 has the light emitting element 112, the polarizing plate 114, and the phase difference plate 116, and the measuring unit 120 does not have the phase difference plate and has the polarizing plate 124 and the light receiving element 122. Alternatively, the configuration may be that the light source 110 does not have the phase difference plate and has the light emitting element 112 and the polarizing plate 114, and the measuring unit 120 has the phase difference plate 126, the polarizing plate 124, and the light receiving element 122. That is, the configuration may be that the light source 110 has the light emitting element 112 and the polarizing plate 114 and the measuring unit 120 has the polarizing plate 124 and the light receiving element 122, and one of the light source 110 or the measuring unit 120 has the phase difference plate.

From the viewpoint of measuring the polarization state by the principle of rotation compensator type ellipsometry, it is sufficient that the phase difference plate is disposed on any one of the light source 110 or the measuring unit 120, but in terms of being able to measure up to the Mueller matrix, it is preferable that the phase difference plates are arranged in both the light source 110 and the measuring unit 120.

Hereinbefore, the concentration measuring method of an optically active substance and the concentration measuring device of an optically active substance according to the embodiment of the present invention have been described in detail, but the present invention is not limited to the above-described example and various improvements and changes can be made without departing from the spirit of the present invention.

EXPLANATION OF REFERENCES

10: eye
12, 12a, 12b: cornea
14, 14a, 14b: aqueous humor
16: lens
100: concentration measuring device
110: light source
112: light emitting element
114, 124: polarizing plate
116, 126: phase difference plate
120, 120a~120c: measuring unit
122: light receiving element
122b: two-dimensional sensor
124b: patterned polarizing plate
126a: first phase difference plate
126b: second phase difference plate
130: control unit
140: calculation unit
Sin1: first incidence light
Sin2: second incidence light
Sout1: first reflected light
Sout2: second reflected light
$\theta_1$, $\theta_2$: a
$\theta_i$: incidence angle
N: normal line
H: tangent plane
DA: horizontal direction of tangent plane

What is claimed is:

1. A concentration measuring method of an optically active substance, comprising:
a first step of measuring a polarization state of a first reflected light that is obtained by irradiating an aqueous humor in an eye with a first incidence light which is polarized and reflecting the first incidence light at an interface between the aqueous humor and a lens, in which the polarization state of the first reflected light is measured by performing the irradiation with the first incidence light such that an angle $\theta_1$ between a normal line to a tangent plane at a point where the first incidence light intersects a surface of the lens, and the first incidence light is equal to or smaller than a Brewster angle;
a second step of measuring a polarization state of a second reflected light that is obtained by irradiating the aqueous humor in the eye with a second incidence light which is polarized and reflecting the second incidence light at the interface between the aqueous humor and the lens, in which the polarization state of the second reflected light is measured by performing the irradiation with the second incidence light such that an angle $\theta_2$ between a normal line to a tangent plane at a point where the second incidence light intersects the surface of the lens, and the second incidence light is equal to or larger than the Brewster angle;

a third step of calculating an optical rotation of the aqueous humor with information on the polarization state of the first reflected light, which is obtained in the first step, and information on the polarization state of the second reflected light, which is obtained in the second step; and a fourth step of calculating a concentration of an optically active substance in the aqueous humor from the optical rotation of the aqueous humor.

2. The concentration measuring method of an optically active substance according to claim 1,
wherein the first step is performed a plurality of times under conditions in which the angle $\theta_1$ between the normal line and the first incidence light is different, so that a plurality of pieces of the information on the polarization state of the first reflected light in the first step are acquired, and
the third step is performed with the plurality of pieces of the information acquired.

3. The concentration measuring method of an optically active substance according to claim 1,
wherein the second step is performed a plurality of times under conditions in which the angle $\theta_2$ between the normal line and the second incidence light is different, so that a plurality of pieces of the information on the polarization state of the second reflected light in the second step are acquired, and
the third step is performed with the plurality of pieces of the information acquired.

4. The concentration measuring method of an optically active substance according to claim 1,
wherein the first step is performed a plurality of times while changing a wavelength of the first incidence light, so that a plurality of pieces of the information on the polarization state of the first reflected light in the first step are acquired, and
the third step is performed with the plurality of pieces of the information acquired.

5. The concentration measuring method of an optically active substance according to claim 1,
wherein the second step is performed a plurality of times while changing a wavelength of the second incidence light, so that a plurality of pieces of the information on the polarization state of the second reflected light in the second step are acquired, and
the third step is performed with the plurality of pieces of the information acquired.

6. The concentration measuring method of an optically active substance according to claim 1,
wherein the angle $\theta_2$ between the normal line and the second incidence light in the second step is more than the Brewster angle.

7. The concentration measuring method of an optically active substance according to claim 1,
wherein the optically active substance is glucose.

8. The concentration measuring method of an optically active substance according to claim 1,
wherein, in at least one of the first step or the second step, a two-dimensional sensor in which light receiving sections for receiving the reflected light are two-dimensionally arranged is used.

9. The concentration measuring method of an optically active substance according to claim 1,
wherein, in the third step, information on optical characteristics of a cornea of the eye is acquired with the information on the polarization state of the first reflected light, which is obtained in the first step, and
the optical rotation of the aqueous humor is calculated with the information on the optical characteristics of the cornea and the information on the polarization state of the second reflected light, which is obtained in the second step.

10. A concentration measuring device of an optically active substance, which is for performing the concentration measuring method of an optically active substance according to claim 1, the concentration measuring device comprising:
a light source for irradiating an incidence light which is polarized to an aqueous humor in an eye;
a measuring unit for measuring a polarization state of a reflected light obtained by reflecting the incidence light at an interface between the aqueous humor and a lens;
a control unit for controlling an incidence angle of the incidence light; and
a calculation unit for calculating an optical rotation of the aqueous humor using information on the polarization state of the reflected light, which is measured by the measuring unit.

11. The concentration measuring device of an optically active substance according to claim 10,
wherein the light source has a light emitting element and a polarizing plate,
the measuring unit has a polarizing plate and a light receiving element, and
at least one of the light source or the measuring unit has a phase difference plate.

12. The concentration measuring device of an optically active substance according to claim 11,
wherein the light receiving element has a two-dimensional sensor in which light receiving sections for receiving the reflected light are two-dimensionally arranged.

13. The concentration measuring method of an optically active substance according to claim 2,
wherein the second step is performed a plurality of times under conditions in which the angle $\theta_2$ between the normal line and the second incidence light is different, so that a plurality of pieces of the information on the polarization state of the second reflected light in the second step are acquired, and
the third step is performed with the plurality of pieces of the information acquired.

14. The concentration measuring method of an optically active substance according to claim 2,
wherein the first step is performed a plurality of times while changing a wavelength of the first incidence light, so that a plurality of pieces of the information on the polarization state of the first reflected light in the first step are acquired, and
the third step is performed with the plurality of pieces of the information acquired.

15. The concentration measuring method of an optically active substance according to claim 2,
wherein the second step is performed a plurality of times while changing a wavelength of the second incidence light, so that a plurality of pieces of the information on the polarization state of the second reflected light in the second step are acquired, and
the third step is performed with the plurality of pieces of the information acquired.

16. The concentration measuring method of an optically active substance according to claim 2, wherein the angle $\theta_2$ between the normal line and the second incidence light in the second step is more than the Brewster angle.

17. The concentration measuring method of an optically active substance according to claim 2, wherein the optically active substance is glucose.

18. The concentration measuring method of an optically active substance according to claim 2, wherein, in at least one of the first step or the second step, a two-dimensional sensor in which light receiving sections for receiving the reflected light are two-dimensionally arranged is used.

19. The concentration measuring method of an optically active substance according to claim 2, wherein, in the third step, information on optical characteristics of a cornea of the eye is acquired with the information on the polarization state of the first reflected light, which is obtained in the first step, and the optical rotation of the aqueous humor is calculated with the information on the optical characteristics of the cornea and the information on the polarization state of the second reflected light, which is obtained in the second step.

20. A concentration measuring device of an optically active substance, which is for performing the concentration measuring method of an optically active substance according to claim 2, the concentration measuring device comprising:

a light source for irradiating an incidence light which is polarized to an aqueous humor in an eye;

a measuring unit for measuring a polarization state of a reflected light obtained by reflecting the incidence light at an interface between the aqueous humor and a lens;

a control unit for controlling an incidence angle of the incidence light; and a calculation unit for calculating an optical rotation of the aqueous humor using information on the polarization state of the reflected light, which is measured by the measuring unit.

\* \* \* \* \*